(12) United States Patent
Whitfield et al.

(10) Patent No.: US 8,968,337 B2
(45) Date of Patent: Mar. 3, 2015

(54) ARTICULATING CLIP APPLIER

(75) Inventors: Kenneth Whitfield, North Haven, CT (US); Csaba L. Rethy, Fairfield, CT (US)

(73) Assignee: Covidien LP, Mansfield, MA (US)

( * ) Notice: Subject to any disclaimer, the term of this patent is extended or adjusted under 35 U.S.C. 154(b) by 377 days.

(21) Appl. No.: 13/151,388

(22) Filed: Jun. 2, 2011

(65) Prior Publication Data
US 2012/0029534 A1 Feb. 2, 2012

Related U.S. Application Data

(60) Provisional application No. 61/368,349, filed on Jul. 28, 2010.

(51) Int. Cl.
*A61B 17/10* (2006.01)
*A61B 17/128* (2006.01)
*A61B 17/29* (2006.01)

(52) U.S. Cl.
CPC ..... *A61B 17/1285* (2013.01); *A61B 2017/2927* (2013.01); *A61B 2017/2943* (2013.01)
USPC .......................................... 606/143; 606/142

(58) Field of Classification Search
USPC ......... 606/139, 142, 143, 151, 205–207, 219; 227/175.1, 176.1, 901; 600/146
See application file for complete search history.

(56) References Cited

U.S. PATENT DOCUMENTS

| | | |
|---|---|---|
| 3,120,230 A | 2/1964 | Skold |
| 3,638,847 A | 2/1972 | Noiles et al. |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |

(Continued)

FOREIGN PATENT DOCUMENTS

| | | |
|---|---|---|
| DE | 20 2009 006113 | 7/2009 |
| EP | 0 085 931 A2 | 8/1983 |

(Continued)

OTHER PUBLICATIONS

Extended European Search Report corresponding to European Application No. EP 11250214.1, completed May 25, 2011; mailed Jun. 1, 2011; (3 Pages).

(Continued)

*Primary Examiner* — Elizabeth Houston
*Assistant Examiner* — Robert Lynch

(57) ABSTRACT

A surgical apparatus for application of surgical clips to body tissue is provided. The surgical apparatus includes a housing, a drive assembly, a trigger, and a shaft assembly. The trigger is operatively connected with the drive assembly. The drive assembly is at least partially positioned within the housing. The shaft assembly extends distally from the housing and has a first tubular member pivotally connected with a second tubular member located distally from the first tubular member. An articulation mechanism is operatively connected between the first and second tubular members, and includes a gear rack, at least one gear, and a gear segment, respectfully connected with each other to pivot the second tubular member about the pivot axis. The gear rack and at least one gear are located within the first tubular member. The gear segment extends proximally from the second tubular member.

18 Claims, 31 Drawing Sheets

(56) References Cited

U.S. PATENT DOCUMENTS

| | | |
|---|---|---|
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,262,587 A | 11/1993 | Moser |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen |
| 5,354,306 A | 10/1994 | Garvey, III et al. |
| 5,364,002 A | 11/1994 | Green et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |
| 5,382,254 A | 1/1995 | McGarry |
| 5,382,255 A | 1/1995 | Castro |
| 5,383,881 A | 1/1995 | Green |
| 5,395,375 A | 3/1995 | Turkel et al. |
| 5,395,381 A | 3/1995 | Green |
| 5,403,327 A | 4/1995 | Thornton et al. |
| 5,409,498 A | 4/1995 | Braddock et al. |
| 5,413,584 A | 5/1995 | Scjulze |
| 5,423,835 A | 6/1995 | Green |
| 5,425,740 A | 6/1995 | Hutchinson, Jr. |
| 5,431,667 A | 7/1995 | Thompson |
| 5,431,668 A | 7/1995 | Burbank, III et al. |
| 5,431,669 A | 7/1995 | Thompson |
| 5,439,468 A | 8/1995 | Schulze et al. |
| 5,441,509 A | 8/1995 | Vidal |
| 5,447,513 A | 9/1995 | Davison et al. |

(56) References Cited

U.S. PATENT DOCUMENTS

| | | |
|---|---|---|
| 5,449,365 A | 9/1995 | Green |
| 5,462,555 A | 10/1995 | Bolanos |
| 5,462,558 A | 10/1995 | Kolesa |
| 5,464,416 A | 11/1995 | Steckel |
| 5,474,566 A | 12/1995 | Alesi |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips |
| 5,514,149 A | 5/1996 | Green |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green |
| 5,527,320 A | 6/1996 | Carruthers et al. |
| 5,542,949 A | 8/1996 | Yoon |
| 5,547,474 A | 8/1996 | Kloeckl |
| 5,569,274 A | 10/1996 | Rapacki et al. |
| 5,571,121 A | 11/1996 | Heifetz |
| 5,575,799 A | 11/1996 | Bolanos et al. |
| 5,575,802 A | 11/1996 | McQuildin et al. |
| 5,582,615 A | 12/1996 | Foshee et al. |
| 5,584,840 A | 12/1996 | Ramsey et al. |
| 5,588,581 A | 12/1996 | Conlon et al. |
| 5,591,178 A | 1/1997 | Green et al. |
| 5,593,414 A | 1/1997 | Shipp et al. |
| 5,593,421 A | 1/1997 | Bauer |
| 5,601,224 A | 2/1997 | Bishop et al. |
| 5,601,573 A | 2/1997 | Fogelberg et al. |
| 5,601,574 A | 2/1997 | Stefanchik et al. |
| 5,607,436 A | 3/1997 | Pratt |
| 5,618,291 A | 4/1997 | Thompson |
| 5,618,306 A | 4/1997 | Roth et al. |
| 5,620,452 A | 4/1997 | Yoon |
| 5,626,585 A | 5/1997 | Mittelstadt |
| 5,626,586 A | 5/1997 | Pistl et al. |
| 5,626,587 A | 5/1997 | Bishop et al. |
| 5,626,592 A | 5/1997 | Phillips |
| RE35,525 E | 6/1997 | Stefanchik et al. |
| 5,634,584 A | 6/1997 | Okorocha et al. |
| 5,634,930 A | 6/1997 | Thornton et al. |
| 5,643,291 A | 7/1997 | Pier |
| 5,645,551 A | 7/1997 | Green |
| 5,645,553 A | 7/1997 | Kolesa |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier |
| 5,695,505 A | 12/1997 | Yoon |
| 5,697,938 A | 12/1997 | Jensen et al. |
| 5,700,270 A | 12/1997 | Peyser |
| 5,700,271 A | 12/1997 | Whitfield |
| 5,702,048 A | 12/1997 | Eberlin |
| 5,709,706 A | 1/1998 | Kienzle et al. |
| 5,713,911 A | 2/1998 | Racenet |
| 5,713,912 A | 2/1998 | Porter |
| 5,720,756 A | 2/1998 | Green |
| 5,722,982 A | 3/1998 | Ferreira et al. |
| 5,725,537 A | 3/1998 | Green |
| 5,725,538 A | 3/1998 | Green |
| 5,725,542 A | 3/1998 | Yoon |
| 5,733,295 A | 3/1998 | Back et al. |
| 5,755,726 A | 5/1998 | Pratt |
| 5,766,189 A | 6/1998 | Matsuno |
| 5,769,857 A | 6/1998 | Reztzov et al. |
| 5,772,673 A | 6/1998 | Cuny |
| 5,772,693 A | 6/1998 | Brownlee |
| 5,776,146 A | 7/1998 | Sackier et al. |
| 5,776,147 A | 7/1998 | Dolendo |
| 5,779,718 A | 7/1998 | Green |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts |
| 5,792,150 A | 8/1998 | Pratt |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,833,695 A | 11/1998 | Yoon |
| 5,833,696 A | 11/1998 | Whitfield |
| 5,833,700 A | 11/1998 | Fogelberg et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser |
| 5,868,761 A | 2/1999 | Nicholas |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare |
| 5,913,862 A | 6/1999 | Ramsey et al. |
| 5,918,791 A | 7/1999 | Sorrentino et al. |
| 5,921,996 A | 7/1999 | Sherman |
| 5,921,997 A | 7/1999 | Fogelberg et al. |
| 5,928,251 A | 7/1999 | Aranyi |
| 5,938,667 A | 8/1999 | Peyser |
| 5,951,574 A | 9/1999 | Stefanchik et al. |
| 5,972,003 A | 10/1999 | Rousseau |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| RE36,720 E | 5/2000 | Green |
| 6,059,799 A | 5/2000 | Aranyi |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis |
| 6,537,289 B1 | 3/2003 | Kayan |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |

(56) References Cited

U.S. PATENT DOCUMENTS

| | | |
|---|---|---|
| 6,652,539 B2 | 11/2003 | Shipp et al. |
| 6,673,083 B1 | 1/2004 | Kayan |
| 6,676,659 B2 | 1/2004 | Hutchins et al. |
| 6,679,894 B2 | 1/2004 | Damarati |
| RE38,445 E | 2/2004 | Pistl |
| 6,695,854 B1 | 2/2004 | Kayan |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,140,528 B2 | 11/2006 | Shelton, IV |
| 7,143,925 B2 | 12/2006 | Shelton, IV et al. |
| 7,144,402 B2 | 12/2006 | Kuester, III |
| 7,147,138 B2 | 12/2006 | Shelton, IV |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et |
| 7,211,092 B2 | 5/2007 | Hughett |
| 7,213,736 B2 | 5/2007 | Wales et al. |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,380,696 B2 | 6/2008 | Shelton, IV et al. |
| 7,404,509 B2 | 7/2008 | Ortiz et al. |
| 7,407,077 B2 | 8/2008 | Ortiz et al. |
| 7,410,086 B2 | 8/2008 | Ortiz et al. |
| 7,487,899 B2 | 2/2009 | Shelton, IV et al. |
| 7,510,562 B2 | 3/2009 | Lindsay |
| 7,513,408 B2 | 4/2009 | Shelton, IV et al. |
| 7,637,917 B2 | 12/2009 | Whitfield |
| 7,681,772 B2 | 3/2010 | Green et al. |
| 7,695,482 B2 | 4/2010 | Viola |
| 7,717,926 B2 | 5/2010 | Whitfield |
| 7,819,886 B2 | 10/2010 | Whitfield |
| 7,887,553 B2 | 2/2011 | Lehman et al. |
| 7,905,890 B2 | 3/2011 | Whitfield |
| 7,988,027 B2 | 8/2011 | Olson |
| 8,011,550 B2 | 9/2011 | Aranyi |
| 8,011,555 B2 | 9/2011 | Tarinelli |
| 8,016,178 B2 | 9/2011 | Olson |
| 8,021,375 B2 | 9/2011 | Aldrich |
| 8,021,378 B2 | 9/2011 | Sixto, Jr. |
| 8,056,565 B2 | 11/2011 | Zergiebel |
| 8,070,760 B2 | 12/2011 | Fujita |
| 8,083,668 B2 | 12/2011 | Durgin |
| 8,088,061 B2 | 1/2012 | Wells |
| 8,091,755 B2 | 1/2012 | Kayan |
| 8,128,643 B2 | 3/2012 | Aranyi |
| 8,142,451 B2 | 3/2012 | Boulnois |
| 8,157,149 B2 | 4/2012 | Olson |
| 8,157,151 B2 | 4/2012 | Ingmanson |
| 8,216,257 B2 | 7/2012 | Huitema |
| 8,236,012 B2 | 8/2012 | Molitor |
| 8,246,634 B2 | 8/2012 | Huitema |
| 8,246,635 B2 | 8/2012 | Huitema |
| 8,262,679 B2 | 9/2012 | Nguyen |
| 8,267,944 B2 | 9/2012 | Sorrentino |
| 8,267,945 B2 | 9/2012 | Nguyen |
| 8,267,946 B2 | 9/2012 | Whitfield |
| 8,282,655 B2 | 10/2012 | Whitfield |
| 8,328,822 B2 | 12/2012 | Huitema |
| 8,336,556 B2 | 12/2012 | Zergiebel |
| 8,348,130 B2 | 1/2013 | Shah |
| 8,357,171 B2 | 1/2013 | Whitfield |
| 8,371,491 B2 | 2/2013 | Huitema |
| 8,382,773 B2 | 2/2013 | Whitfield |
| 8,403,945 B2 | 3/2013 | Whitfield |
| 8,403,946 B2 | 3/2013 | Whitfield |
| 8,409,222 B2 | 4/2013 | Whitfield |
| 8,409,223 B2 | 4/2013 | Sorrentino |
| 8,419,752 B2 | 4/2013 | Sorrentino |
| 8,430,892 B2 | 4/2013 | Bindra |
| 8,444,660 B2 | 5/2013 | Adams |
| 8,465,502 B2 | 6/2013 | Zergiebel |

(56) References Cited

U.S. PATENT DOCUMENTS

| | | |
|---|---|---|
| 8,475,473 B2 | 7/2013 | Vandenbroek |
| 8,480,688 B2 | 7/2013 | Boulnois |
| 8,486,091 B2 | 7/2013 | Sorrentino |
| 8,491,608 B2 | 7/2013 | Sorrentino |
| 8,496,673 B2 | 7/2013 | Nguyen |
| 8,506,580 B2 | 8/2013 | Zergiebel |
| 8,512,357 B2 | 8/2013 | Viola |
| 8,523,882 B2 | 9/2013 | Huitema |
| 8,529,585 B2 | 9/2013 | Jacobs |
| 8,529,586 B2 | 9/2013 | Rosenberg |
| 8,529,588 B2 | 9/2013 | Ahlberg |
| 8,545,486 B2 | 10/2013 | Malkowski |
| 8,579,918 B2 | 11/2013 | Whitfield |
| 8,585,717 B2 | 11/2013 | Sorrentino |
| 8,603,109 B2 | 12/2013 | Aranyi |
| 8,734,469 B2 | 5/2014 | Pribanic et al. |
| 8,747,423 B2 | 6/2014 | Whitfield et al. |
| 8,814,884 B2 | 8/2014 | Whitfield et al. |
| 8,845,659 B2 | 9/2014 | Whitfield et al. |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2004/0193213 A1 | 9/2004 | Aranyi |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson, Jr. et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |

(56) References Cited

U.S. PATENT DOCUMENTS

| | | |
|---|---|---|
| 2007/0073314 A1 | 3/2007 | Gadberry et al. |
| 2007/0083218 A1 | 4/2007 | A. Morris |
| 2007/0093856 A1 | 4/2007 | Whitfield |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto, Jr. et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0243145 A1* | 10/2008 | Whitfield et al. ............. 606/143 |
| 2009/0101692 A1* | 4/2009 | Whitman et al. .......... 227/175.1 |
| 2010/0057105 A1 | 3/2010 | Sorrentino |
| 2010/0057107 A1 | 3/2010 | Sorrentino et al. |
| 2010/0274262 A1 | 10/2010 | Schulz et al. |
| 2010/0274264 A1 | 10/2010 | Schulz et al. |
| 2011/0087242 A1 | 4/2011 | Pribanic |
| 2011/0137323 A1 | 6/2011 | Malkowski |
| 2011/0208212 A1 | 8/2011 | Zergiebel |
| 2011/0224701 A1 | 9/2011 | Menn |
| 2011/0245847 A1 | 10/2011 | Menn |
| 2012/0029534 A1 | 2/2012 | Whitfield |
| 2012/0109158 A1 | 5/2012 | Zammataro |
| 2012/0116420 A1 | 5/2012 | Sorrentino |
| 2012/0123446 A1 | 5/2012 | Aranyi |
| 2012/0197269 A1 | 8/2012 | Zammataro |
| 2012/0265220 A1 | 10/2012 | Menn |
| 2012/0277765 A1 | 11/2012 | Zammataro |
| 2012/0330326 A1 | 12/2012 | Creston |
| 2013/0110135 A1 | 5/2013 | Whitfield |
| 2013/0131697 A1 | 5/2013 | Hartoumbekis |
| 2013/0165952 A1 | 6/2013 | Whitfield |
| 2013/0172910 A1 | 7/2013 | Malkowski |
| 2013/0172911 A1 | 7/2013 | Rockrohr |
| 2013/0172912 A1 | 7/2013 | Whitfield |
| 2013/0190779 A1 | 7/2013 | Whitfield |
| 2013/0190780 A1 | 7/2013 | Whitfield |
| 2013/0253541 A1 | 9/2013 | Zergiebel |
| 2013/0274767 A1 | 10/2013 | Sorrentino |
| 2013/0289583 A1 | 10/2013 | Zergiebel |
| 2013/0296891 A1 | 11/2013 | Hartoumbekis |
| 2013/0296892 A1 | 11/2013 | Sorrentino |
| 2013/0310849 A1 | 11/2013 | Malkowski |
| 2013/0325040 A1 | 12/2013 | Zammataro |
| 2014/0039526 A1 | 2/2014 | Malkowski |
| 2014/0052157 A1 | 2/2014 | Whitfield |
| 2014/0058412 A1 | 2/2014 | Aranyi |
| 2014/0194903 A1 | 7/2014 | Malkowski et al. |
| 2014/0207156 A1 | 7/2014 | Malkowski |

FOREIGN PATENT DOCUMENTS

| | | |
|---|---|---|
| EP | 0 086 721 | 8/1983 |
| EP | 0 089 737 A1 | 9/1983 |
| EP | 0 324 166 A2 | 7/1989 |
| EP | 0 392 750 A1 | 10/1990 |
| EP | 0 409 569 A1 | 1/1991 |
| EP | 0 569 223 | 11/1993 |
| EP | 0 594 003 | 4/1994 |
| EP | 0 598 529 A2 | 5/1994 |
| EP | 0 769 275 A1 | 5/1994 |
| EP | 0 685 204 A1 | 12/1995 |
| EP | 0 732 078 A2 | 9/1996 |
| EP | 0 755 655 A2 | 1/1997 |
| EP | 0 769 274 | 4/1997 |
| EP | 0 769 274 AI | 4/1997 |
| EP | 0 769 275 A1 | 4/1997 |
| EP | 0 834 286 A1 | 4/1998 |
| EP | 1 317 906 A1 | 6/2003 |
| EP | 1 609 427 A1 | 12/2005 |
| EP | 1 712 187 | 10/2006 |
| EP | 1 712 191 A2 | 10/2006 |
| EP | 1 757 236 | 2/2007 |
| EP | 1 813 199 A1 | 8/2007 |
| EP | 1 908 423 | 4/2008 |
| EP | 1 908 423 A2 | 4/2008 |
| EP | 1 913 881 A1 | 4/2008 |
| EP | 2 229 895 A1 | 9/2010 |
| EP | 2 332 471 | 6/2011 |
| JP | 2003 033361 A | 2/2003 |
| WO | WO 01/66001 | 9/2001 |
| WO | WO 01/67965 | 9/2001 |
| WO | WO 03/086207 | 10/2003 |
| WO | WO 03/092473 | 11/2003 |
| WO | WO 2005/091457 A1 | 9/2005 |
| WO | WO 2006/042076 | 4/2006 |
| WO | WO 2006/042076 A2 | 4/2006 |
| WO | WO 2006/042084 A2 | 4/2006 |
| WO | WO 2006/042110 | 4/2006 |
| WO | WO 2006/042110 A2 | 4/2006 |
| WO | WO 2006/042141 | 4/2006 |
| WO | WO 2006/135479 | 12/2006 |
| WO | WO 2008/116928 | 10/2008 |
| WO | WO 2008/118928 A2 | 10/2008 |
| WO | WO 2008/127968 | 10/2008 |
| WO | WO 2008/127968 A2 | 10/2008 |

OTHER PUBLICATIONS

Extended International Search Report corresponding to European Application No. 07 25 3905.9, completed Jan. 29, 2008; mailed Feb. 7, 2008; (7 Pages).

Partial International Search Report corresponding to European Application No. EP 07 25 3807.7, completed Jul. 23, 2008; mailed Aug. 1, 2008; (3 pages).

International Search Report corresponding to International Application No. PCT/US08/58185, completed Sep. 4, 2008; mailed Sep. 9, 2008; (2 Pages).

International Search Report corresponding to International Application No. PCT/US08/59859, completed Sep. 14, 2008; mailed Sep. 18, 2008; (2 Pages).

Extended European Search Report corresponding to European Application No. EP 07 25 3807.7, completed Nov. 7, 2008; mailed Nov. 26, 2008; (11 Pages).

Extended European Search Report corresponding to European Application No. EP 09252049.3, completed Dec. 11, 2009; mailed Jan. 12, 2010; (3 Pages).

Extended European Search Report corresponding to European Application No. EP 09252050.1, completed Dec. 23, 2009; mailed Jan. 21, 2010; (3 Pages).

Extended European Search Report corresponding to European Application No. EP 09252051.9, completed Dec. 21, 2009; mailed Jan. 28, 2010; (3 Pages).

Extended European Search Report corresponding to European Application No. EP 09252052.7, completed Nov. 16, 2009; mailed Nov. 24, 2009; (3 Pages).

(56) References Cited

OTHER PUBLICATIONS

Extended European Search Report corresponding to European Application No. EP 09252053.5, completed Nov. 24, 2009; mailed Dec. 1, 2009; (3 Pages).
Extended European Search Report corresponding to European Application No. EP 09252054.3, completed Jan. 7, 2010; mailed Jan. 22, 2010; (3 Pages).
Extended European Search Report corresponding to European Application No. EP 09252056.8, completed Jan. 8, 2010; mailed Feb. 5, 2010; (3 Pages).
Extended European Search Report corresponding to European Application No. EP 10250497.4, completed May 4, 2010; mailed May 12, 2010; (6 Pages).
Extended European Search Report corresponding to European Application No. EP 10252079.8, completed Mar. 8, 2011; mailed Mar. 17, 2011; (3 Pages).
Extended European Search Report corresponding to European Application No. EP 11002681.2, completed May 31, 2011; mailed Jun. 10, 2011; (3 Pages).
European Search Report corresponding to European Application No. EP 05810218.7, completed Apr. 18, 2011; mailed May 20, 2011; (3 pages).
European Search Report corresponding to European Application No. EP 05807612.6, completed May 2, 2011; mailed May 20, 2011; (3 pages).
Extended European Search Report corresponding to European Application No. EP 10251737.2, completed May 9, 2011; mailed May 20, 2011; (4 pages).
"Salute II Disposable Fixation Device", Technique Guide—Laparoscopic and Open Inguinal and Ventral Hernia Repair; Davol, A Bard Company, 2006; (7 Pages).
Extended European Search Report corresponding to European Application No. EP 12 16 2288.0, completed Jun. 4, 2012 and mailed Jul. 7, 2012; (6 Pages).
Extended European Search Report corresponding to European Application No. EP 12 16 5891.8, completed Jun. 12, 2012 and mailed Jun. 20, 2012; (6 Pages).
Extended European Search Report corresponding to European Application No. EP 12 16 4955.2, completed Aug. 23, 2012 and mailed Sep. 4, 2012; (5 Pages).
European Search Report corresponding to European Application No. EP 05 80 2686.5, completed Jan. 9, 2012; mailed Jan. 18, 2012; (3 Pages).
Extended European Search Report corresponding to European Application No. EP 12 15 1313.9, completed Mar. 20, 2012 and mailed Apr. 12, 2012; (5 Pages).
Extended European Search Report corresponding to European Application No. EP 12 16 1291.5, completed Apr. 24, 2012 and mailed May 4, 2012; (5 Pages).
Extended European Search Report corresponding to European Application No. EP 12 18 6401.1, completed Nov. 22, 2012 and mailed Nov. 30, 2012.
Extended European Search Report corresponding to European Application No. EP 12 18 6448.2, completed Nov. 28, 2012 and mailed Dec. 10, 2012; (6 Pages).
Extended European Search Report corresponding to European Application No. EP 12 19 1706.6, completed Dec. 19, 2012 and mailed Jan. 8, 2013; (6 Pages).
Extended European Search Report corresponding to European Application No. EP 11 25 0754.6, completed Oct. 22, 2012 and mailed Oct. 31, 2012; (6 Pages).
Extended European Search Report corresponding to EP 12 19 8745.7, completed Mar. 19, 2013 and mailed Apr. 11, 2013; (8 pp).
Extended European Search Report corresponding to EP 12 15 2989.5, completed Apr. 9, 2013 and mailed Apr. 18, 2013; (9 pp).
Extended European Search Report corresponding to EP 08 73 2820.9, completed Jul. 2, 2013 and mailed Jul. 9, 2013; (10 pp).
Extended European Search Report corresponding to EP 12 19 1706.6, completed Dec. 19, 2012 and mailed Jan. 8, 2013; (6 pp).
Extended European Search Report corresponding to EP 13 17 2008.8, completed Aug. 14, 2013 and mailed Aug. 28, 2013; (8 pp).
Extended European Search Report corresponding to EP 13 16 6382.5, completed Nov. 19, 2013 and mailed Nov. 28, 2013; (8 pp).
Extended European Search Report corresponding to EP 11 25 0194.5, completed Nov. 25, 2013 and mailed Dec. 3, 2013; (8 pp).
Extended European Search Report corresponding to EP 10 25 1798.4, completed Dec. 12, 2013 and mailed Jan. 2, 2014; (9 pp).
Extended European Search Report corresponding to EP 10 25 2112.7, completed Jul. 29, 2014 and mailed Aug. 5, 2014; (8 pp).
Extended European Search Report corresponding to EP 14 15 1673.2, completed Apr. 25, 2014 and mailed May 8, 2014; (8 pp).

* cited by examiner

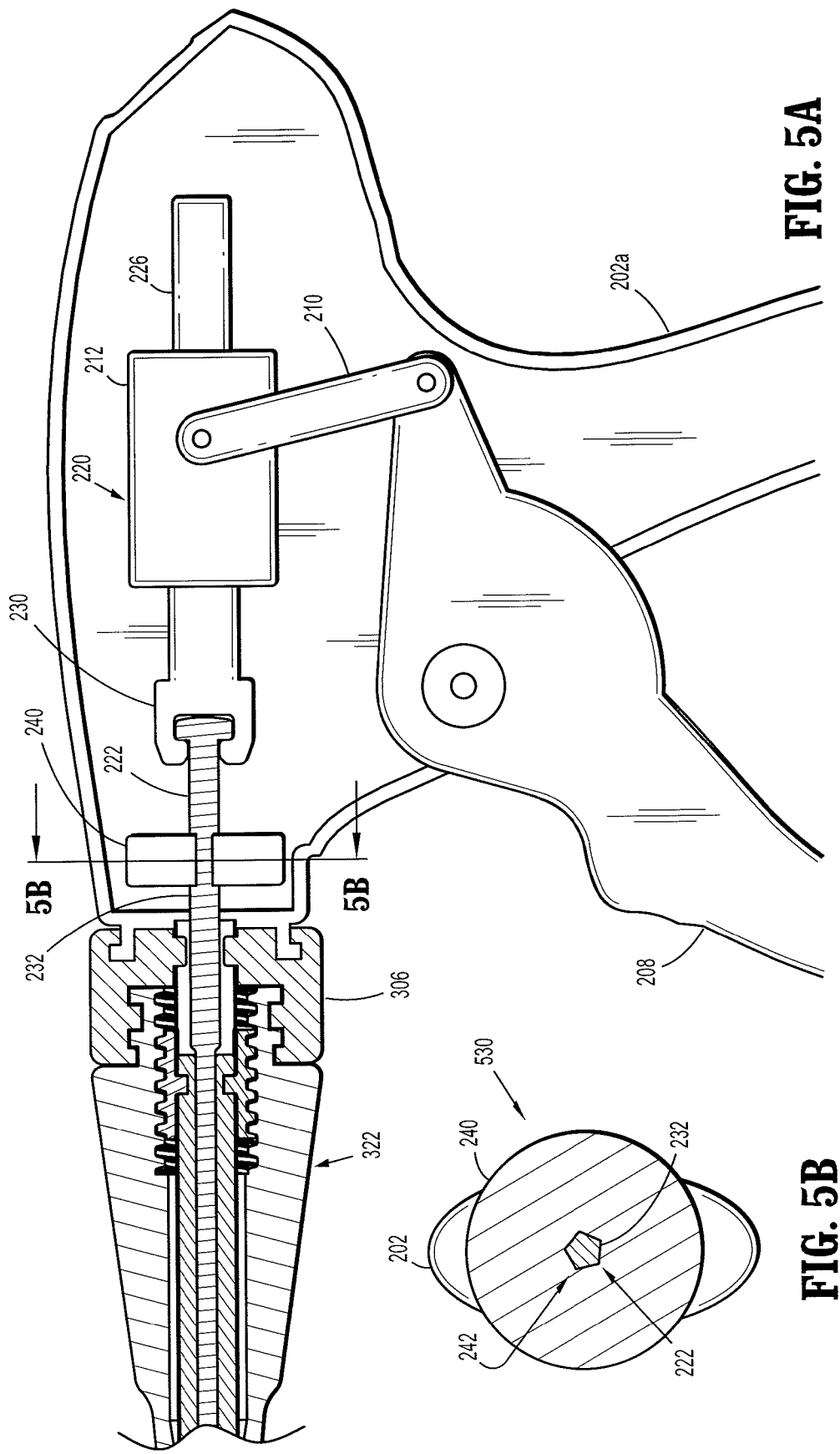

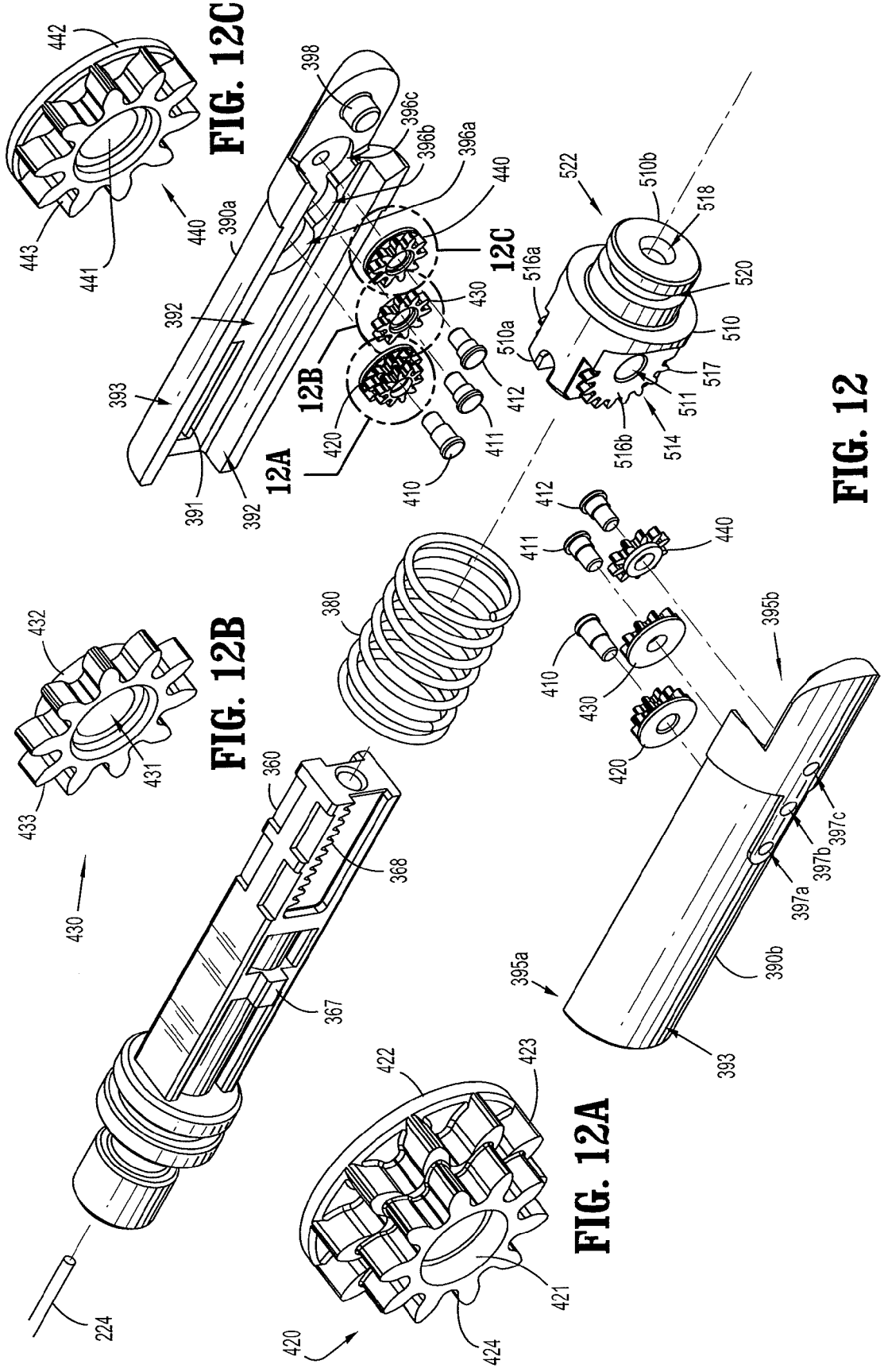

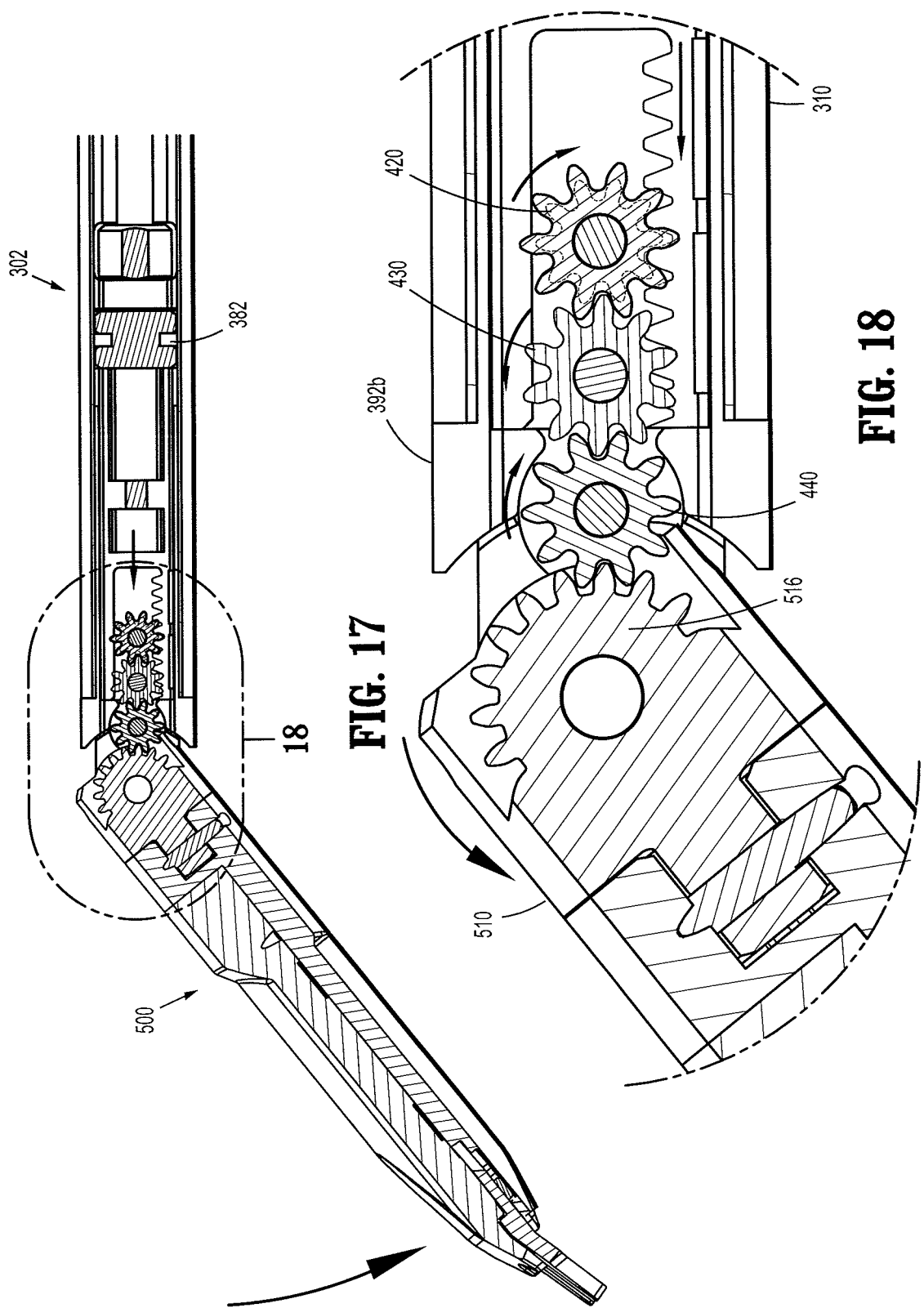

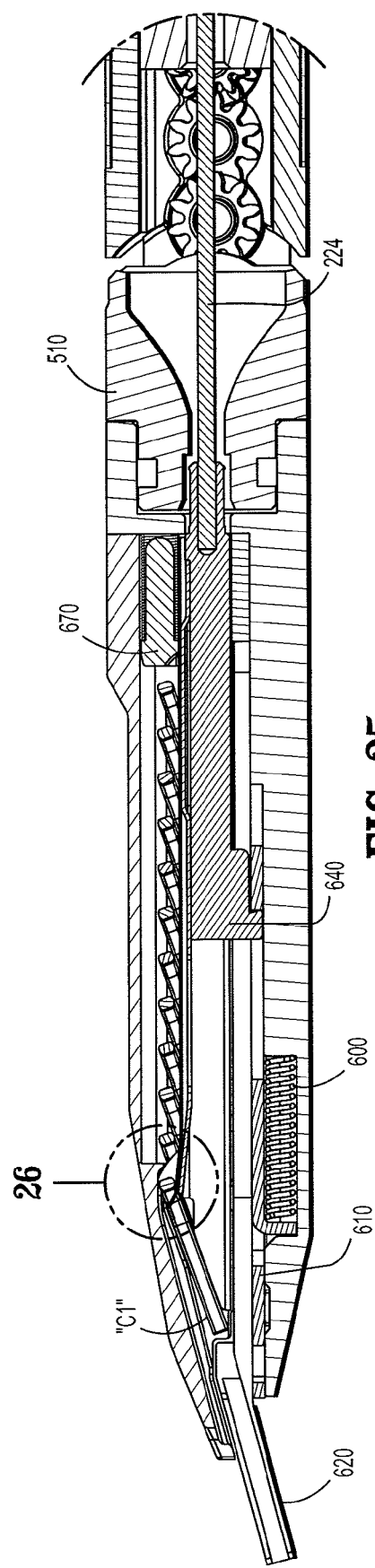
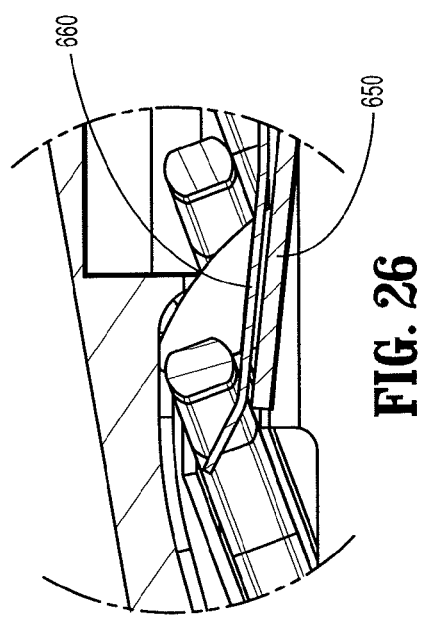
FIG. 25
FIG. 26

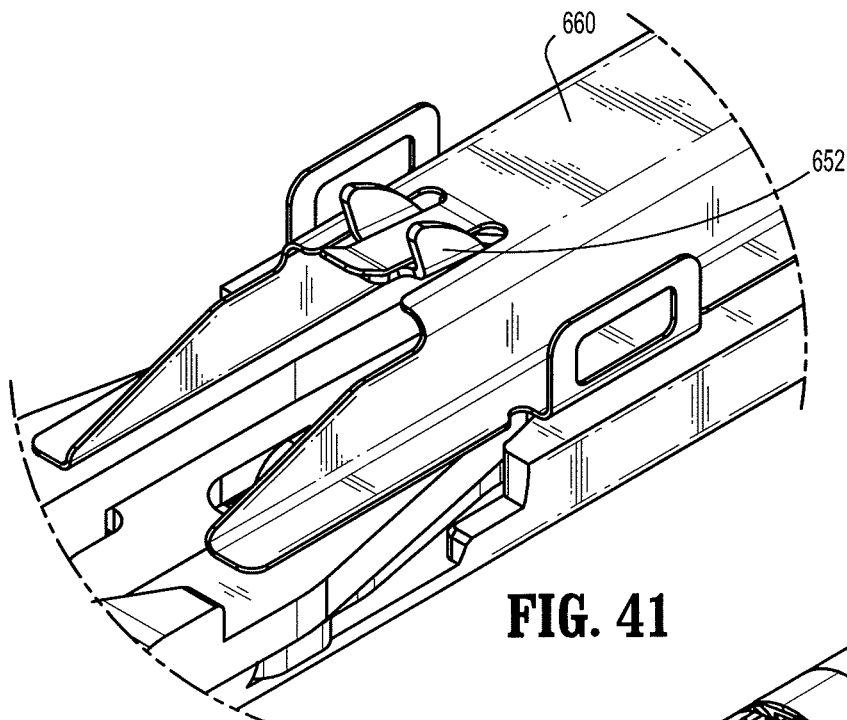
FIG. 41
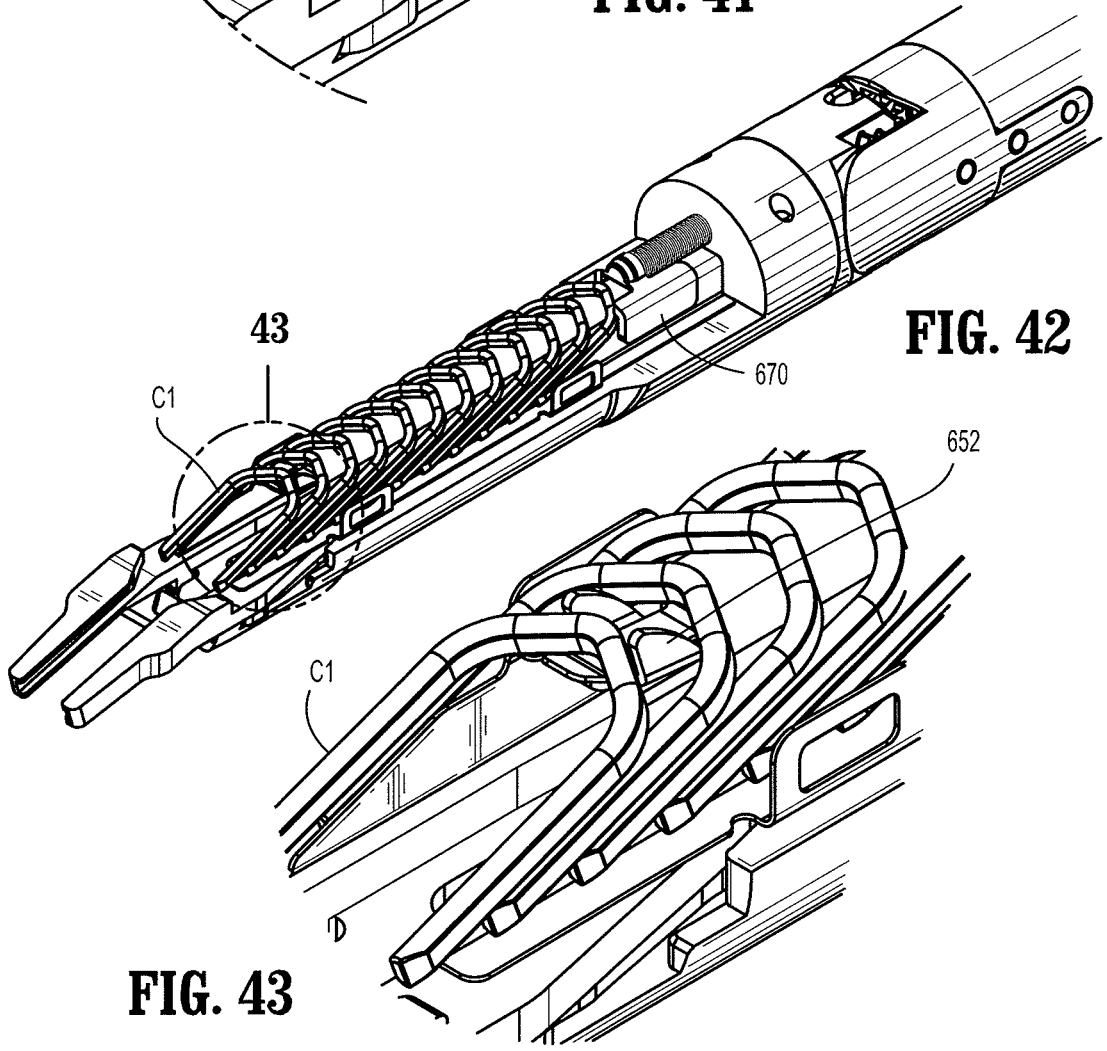
FIG. 42
FIG. 43

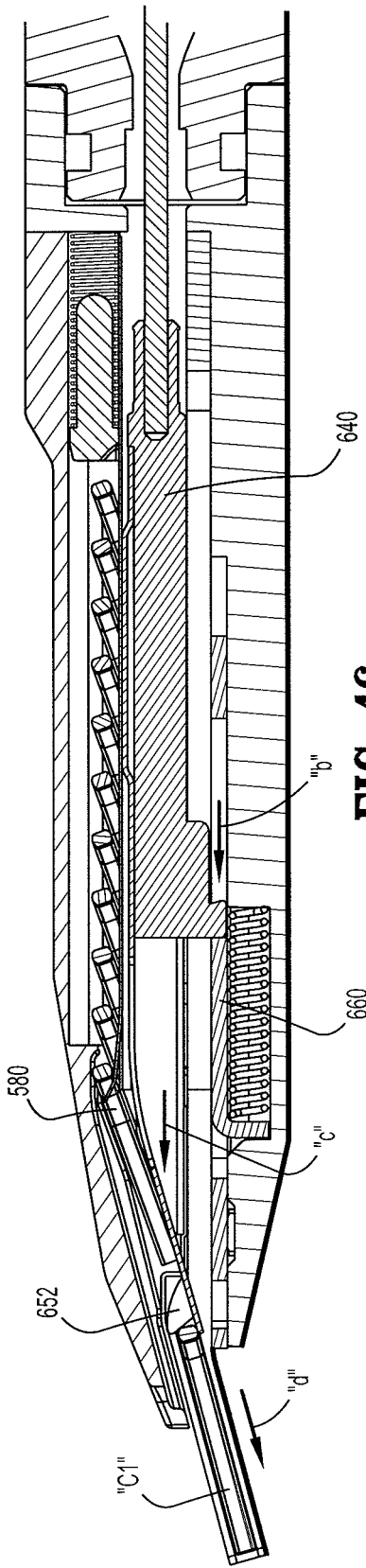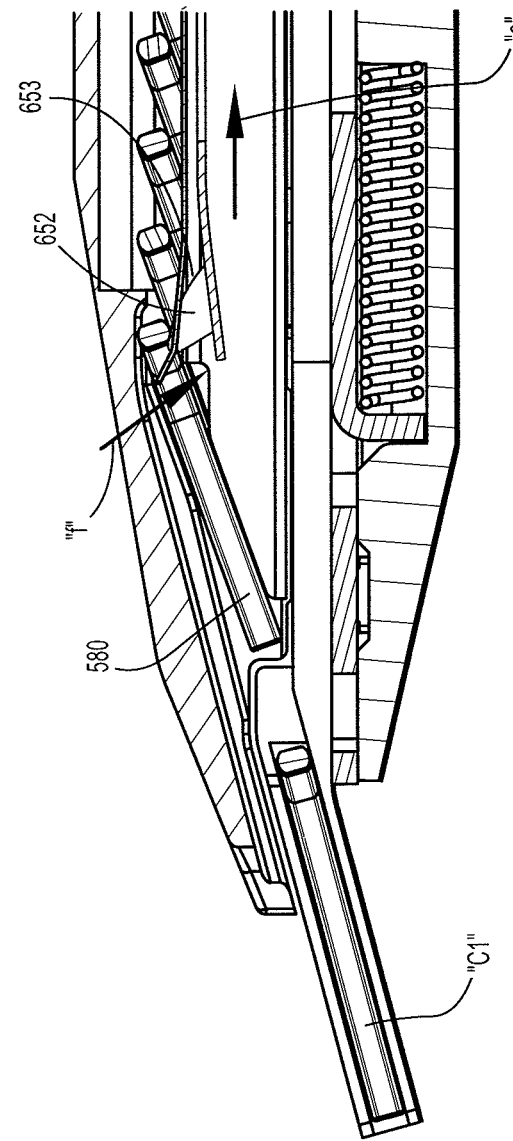
FIG. 46
FIG. 47

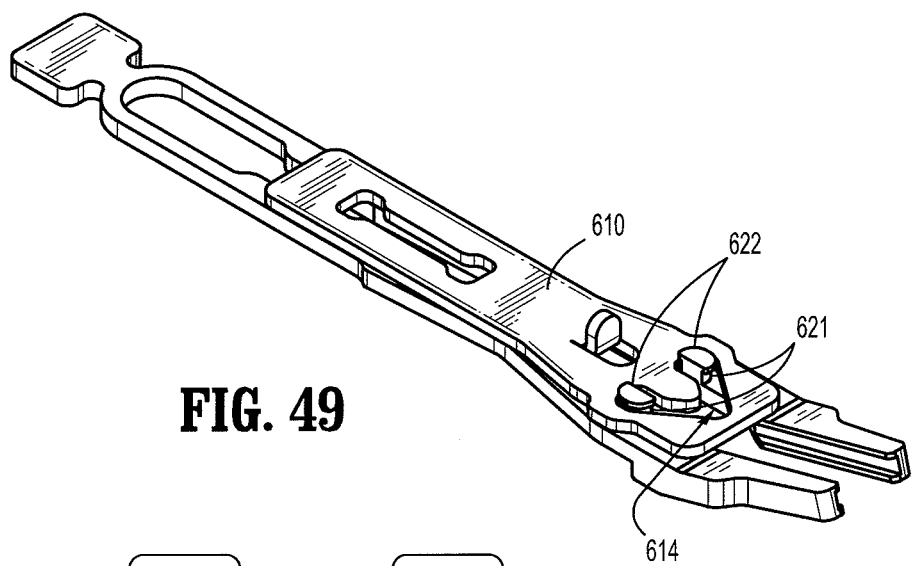
FIG. 49
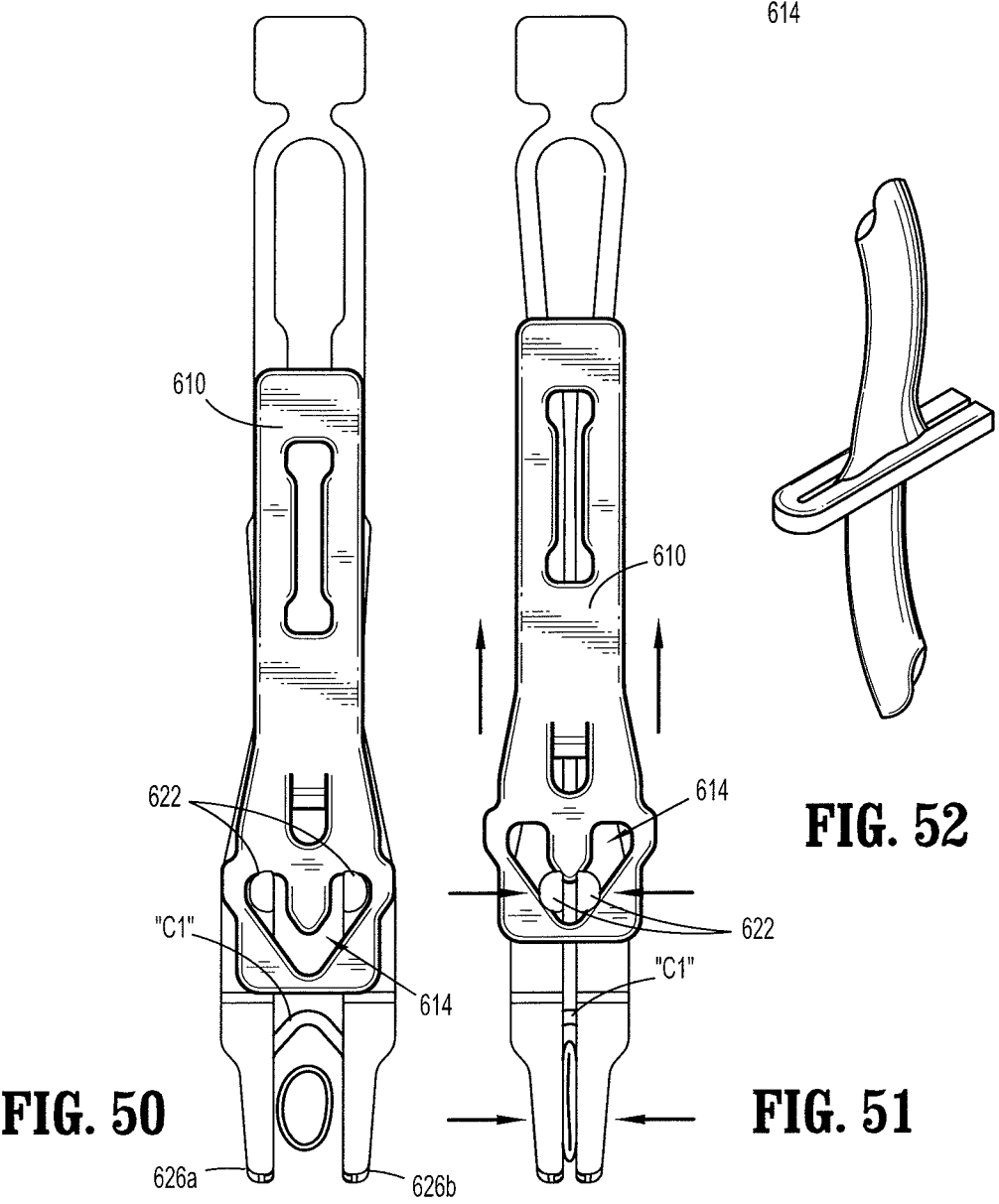
FIG. 50    FIG. 51    FIG. 52

ARTICULATING CLIP APPLIER

CROSS REFERENCE TO RELATED APPLICATION

The present application claims the benefit of and priority to U.S. Provisional Application Ser. No. 61/368,349 filed on Jul. 28, 2010, the entire contents of which are incorporated herein by reference.

BACKGROUND

1. Technical Field

The present disclosure relates to surgical clip appliers and, more particularly, to an articulating endoscopic surgical fastener applier.

2. Background of Related Art

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip during an entry to the body cavity. Such single clip appliers are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly assigned U.S. Pat. Nos. 5,084,057 and 5,100,420 to Green et al., which are both incorporated by reference in their entirety. Another multiple endoscopic clip applier is disclosed in commonly assigned U.S. Pat. No. 5,607,436 to Pratt et al., the contents of which is also hereby incorporated by reference herein in its entirety. These devices are typically, though not necessarily, used during a single surgical procedure. U.S. patent application Ser. No. 08/515,341 now U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine to advance and form multiple clips during a single entry into a body cavity. One significant design goal is that the surgical clip be loaded between the jaws without any compression of the clip from the loading procedure.

Endoscopic or laparoscopic procedures are often performed remotely from the incision. Consequently, application of clips may be complicated by a reduced field of view or reduced tactile feedback for the user at the proximal end of the device. It is therefore desirable to improve the operation of the instrument by providing an instrument that is capable of articulating.

SUMMARY

The present disclosure relates to surgical clip appliers.

According to an aspect of the present disclosure, a surgical apparatus for application of surgical clips to body tissue is provided and includes a housing, a drive assembly, a shaft assembly, and a trigger. The shaft assembly extends distally from the housing. The drive assembly is at least partially positioned within the housing. The trigger is operatively connected to the drive assembly.

The shaft assembly has a first tubular member and a second tubular member located distally from the first tubular member. The first tubular member defines a longitudinal axis. The first tubular member and the second tubular member are pivotally connected through a common pivot axis. The pivot axis is perpendicular to the longitudinal axis. The drive assembly may include a flexible cable that transfers both a translational force and a rotational force from inside of the housing into the second tubular member.

An articulation mechanism operatively connects the first tubular member and the second tubular member. The articulation mechanism includes a gear rack, at least one gear and a gear segment. The gear rack has a plurality of teeth longitudinally placed thereon and is located within the first tubular member. The at least one gear is operatively connected with the gear rack within the first tubular member. The gear segment extends proximally from the second tubular member and is operatively connected with the at least one gear. The gear segment is fixed with respect to the second tubular member. The articulation mechanism pivots the second tubular member about the pivot axis at an angle of up to 90° from the longitudinal axis. The articulating mechanism may include a control knob that is rotatable to pivot the second tubular member.

The second tubular member may include a jaw assembly and a clip cartridge containing a plurality of fasteners disposed therein.

The surgical clip applying apparatus may include a rotation mechanism. The rotation mechanism is operatively connected with and provides a rotational force to the jaw assembly. The rotation mechanism may include a dial and a band. The band is located about a proximal portion of the drive assembly. The dial defines an internal passage and an inner surface. The band defines a contoured outer surface that receives and transmits a rotational force from the inner surface of the dial to the drive assembly. The dial is slidably coupled with the band.

The second tubular member may include two substantially parallel gear segments.

In another embodiment, a surgical apparatus for application of surgical clips to body tissue is provided and includes a housing, a drive assembly, a shaft assembly, and a trigger. The shaft assembly extends distally from the housing.

The shaft assembly has a first tubular member and a second tubular member located distally from the first tubular member. The first tubular member defines a first longitudinal axis, around which the first tubular member may be rotated. The first tubular member and the second tubular member are pivotally connected through a common pivot axis.

The second tubular member defines a second longitudinal axis. A distal portion of the second tubular member is rotatable about the second longitudinal axis. The second tubular member includes a geared segment extending proximally from a proximal portion thereof.

The drive assembly is at least partially positioned within the housing and extends through the first tubular member and partially into the second tubular member. The drive assembly may include a flexible cable to transfer both a translational force and a rotational force from inside of the housing into the second tubular member. The trigger is operatively connected to the drive assembly.

A rack extends along a portion of the longitudinal axis. The rack is located within the first tubular member and reciprocates along the first longitudinal axis. The rack is operatively connected with the geared segment.

The surgical clip applying apparatus may include an articulation mechanism that provides a pivotal force to pivot the second tubular member about the pivot axis at an angle of up to 90° from the first longitudinal axis. The articulating mechanism includes a control knob being rotatable to retract the rack proximally and to extend the rack distally.

The surgical clip applying apparatus may further include a rotation mechanism. The rotation mechanism is operatively connected with the drive assembly to provide a rotational force to the distal portion of the second tubular member. The rotation mechanism includes a dial and a band located about a proximal portion of the drive assembly. The dial defines an internal passage and an inner surface. The band defines a contoured outer surface that is able receive and transmit a rotational force from the inner surface of the dial to the proximal portion of the drive assembly. The dial is slidably coupled with the band.

The second tubular member may include a jaw assembly and a clip cartridge containing a plurality of clips disposed therein. The rotation mechanism may be connected with and provide a rotational force to the jaw assembly.

According to another aspect of the present disclosure, an end effector for operative connection to a surgical handle assembly including an axially reciprocatable drive assembly having a flexible drive cable operatively connected to the end effector is provided. The end effector includes a distal housing portion defining a proximal end, a distal end, and a longitudinal axis; a knuckle portion extending proximally from the proximal end of the distal housing portion, the knuckle portion being bifurcated into a first geared portion and a second geared portion, the distal housing portion being rotatably mounted to the knuckle portion to allow the distal housing portion to rotate about the longitudinal axis with respect to the knuckle portion; a jaw assembly extending distally from the base portion, the jaw assembly including a first jaw and a second jaw movable between a spaced apart position and an approximated position; a plurality of surgical clips loaded in the housing in a partially stacked fashion; and a jaw closure mechanism disposed in the distal housing portion and operatively associated with the jaw assembly and the plurality of surgical clips. A distal end of the flexible drive cable is connected to the jaw closure mechanism so as to transmit an operative force to the jaw closure mechanism when the longitudinal axis of the distal housing portion is either axially aligned or angled with respect to a longitudinal axis of the surgical handle. The jaw closure mechanism feeds a clip into the jaw assembly and forms the fed clip upon a single complete stroke of the flexible drive cable.

The end effector may further include a proximal housing pivotably connected to the knuckle portion; and a gear train supported in the proximal housing. A distal-most gear of the gear train may be operatively engaged with the first geared portion and the second geared portion of the knuckle portion.

The end effector may further include a rack slidably supported in the proximal housing, wherein the rack defines at least one axial row of gear teeth, and wherein the axial row of gear teeth is engaged with a proximal-most gear of the gear train.

In use, axial displacement of the rack relative to the cover results in articulation of the distal housing portion relative to the proximal housing portion.

According to a further aspect of the present disclosure, an end effector for application of surgical clips to body tissue is provided. The end effector includes a portion defining a proximal end, a distal end, and a longitudinal axis; a knuckle portion extending proximally from the proximal end of the base portion, the knuckle portion being bifurcated into a first geared portion and a second geared portion, the base portion being rotatably mounted to the knuckle portion to allow the base portion to rotate about the longitudinal axis with respect to the knuckle portion; a jaw assembly extending distally from the base portion, the jaw assembly including a first jaw and a second jaw movable between a spaced apart position and an approximated position; and a plurality of fasteners located within the base portion, each of the plurality of fasteners having a pair of legs extending from a backspan, each of the plurality of fasteners defining a fastener axis extending in a direction substantially parallel to the pair of legs, each of the plurality of fasteners being arranged within the base portion to form an angle between the fastener axis and the longitudinal axis, each of the plurality of fasteners being located adjacent to another of the plurality of fasteners to form a stack.

The knuckle may include a pivot structure that defines a pivot axis.

The end effector may further include a jaw closure mechanism operatively connected to the jaw assembly, the jaw closure mechanism providing an approximating force to the first jaw and the second jaw.

The knuckle portion may include a plurality of teeth.

The plurality of fasteners may be stacked in a non-colinear position with respect to the second longitudinal axis.

The first jaw and the second jaw may be angled with respect to the longitudinal axis.

The legs of the plurality of fasteners may be disposed in a substantially parallel orientation to the first jaw and the second jaw.

The fasteners may have a U-shape or a V-shape. The stack of fasteners may extend parallel to the longitudinal axis.

The end effector may further include a proximal housing portion connected to knuckle portion such that base portion is pivotable off-axis with respect to the cover. The proximal housing portion may support a gear train in a distal region thereof, and wherein a distal-most gear of the gear train may be operatively engaged with the first geared portion and the second geared portion of the knuckle portion. The end effector may further include a rack slidably supported in a proximal region of the proximal housing portion, wherein the rack defines at least one axial row of gear teeth, and wherein the axial row of gear teeth is engaged with a proximal-most gear of the gear train.

In use, axial displacement of the rack relative to the proximal housing portion may result in articulation of the base portion relative to the proximal housing portion.

According to yet another aspect of the present disclosure, an end effector for operative connection to a surgical handle assembly including an axially reciprocatable drive assembly having a flexible drive cable operatively connected to the end effector is provided. The end effector includes a distal housing portion defining a proximal end, a distal end and a longitudinal axis; a proximal housing portion defining a proximal end, a distal end and a longitudinal axis; a knuckle portion interconnecting the proximal end of the distal housing portion and the distal end of the proximal housing portion, wherein the knuckle portion permits rotation of the distal housing portion relative thereto and articulation of the distal housing portion relative to the proximal housing portion; a jaw assembly supported in the distal end of the distal housing portion, the jaw assembly including a first jaw and a second jaw movable between a spaced apart position and an approximated position; and a plurality of fasteners loaded within the distal housing portion, each of the plurality of fasteners having a pair of legs extending from a backspan, each of the plurality of fasteners defining a fastener axis extending in a direction substantially parallel to the pair of legs, each of the plurality of fasteners being arranged within the base portion such that the fastener axis is disposed at an angle with respect to the longitudinal axis of the distal housing portion, and wherein the plurality of fasteners are arranged in a stack.

The end effector may further include a jaw closure mechanism operatively connected to the jaw assembly, wherein the jaw closure mechanism provides an approximating force to the first jaw and the second jaw upon a proximal movement thereof relative to the first jaw and the second jaw.

The jaw closure mechanism may include a cam plate axially slidably supported in the distal housing portion, wherein the cam plate includes a camming aperture formed therein, wherein the camming aperture has a substantially "V" shaped profile, and wherein each of first jaw and second jaw includes a post extending therefrom and into the camming aperture of the cam plate. In use, movement of the cam plate proximally relative to the first jaw and second jaw engages an edge of the camming aperture against the nubs of the first jaw and the second jaw to approximate the first jaw and the second jaw.

The cam plate may include a protrusion extending distally into the camming aperture; wherein movement of the cam plate distally relative to the first jaw and second jaw engages the protrusion of the camming aperture between the nubs of the first jaw and the second jaw to separate the first jaw and the second jaw.

The flexible drive cable may extend between the distal housing portion and the proximal housing portion, and across the knuckle portion.

A proximal end of the drive cable may be connected to a drive assembly and a distal end of the drive cable may be connected to a block member slidably supported in the base portion, wherein distal movement of the drive cable results in distal movement of the block member to distally advance a feed bar and load a fastener into the jaw assembly.

The end effector may further include a cam plate axially slidably supported in the base portion; wherein the block member includes a finger extending into a proximal axially extending slot provided in the cam plate; wherein the cam plate includes a camming aperture formed therein; wherein the camming aperture has a substantially "V" shaped profile, and wherein each of first jaw and second jaw includes a post extending therefrom and into the camming aperture of the cam plate. In use, distal movement of the block member may result in distal movement of the cam plate and proximal movement of the block member results in proximal movement of the cam plate. Additionally, in use, movement of the cam plate proximally relative to the first jaw and second jaw engages an edge of the camming aperture against the nubs of the first jaw and the second jaw to approximate the first jaw and the second jaw.

The cam plate may include a protrusion extending distally into the camming aperture, wherein movement of the cam plate distally relative to the first jaw and second jaw engages the protrusion of the camming aperture between the nubs of the first jaw and the second jaw to separate the first jaw and the second jaw.

The cam plate may be biased to a distal position.

The end effector may further include a clip follower disposed proximally of the plurality of fasteners, wherein the clip follower is biased in a distal direction to urge the plurality of fasteners distally.

The knuckle portion may be bifurcated into a first geared portion and a second geared portion.

The proximal housing portion may support a gear train in a distal region thereof, and wherein a distal-most gear of the gear train is operatively engaged with the first geared portion and the second geared portion of the knuckle portion.

The end effector may further include a rack slidably supported in a proximal region of the proximal housing portion, wherein the rack defines at least one axial row of gear teeth, and wherein the axial row of gear teeth is engaged with a proximal-most gear of the gear train.

In use, axial displacement of the rack relative to the proximal housing portion results in articulation of the distal housing portion relative to the proximal housing portion such that the longitudinal axis of the distal housing portion is angled with respect to the longitudinal axis of the proximal housing portion.

BRIEF DESCRIPTION OF THE DRAWINGS

The present clip applier will be more fully appreciated as the same becomes better understood from the following detailed description when considered in connection with the following drawings, in which:

FIG. 5A is a cross-sectional side view of a body of the surgical clip applier of FIGS. 1-5, as taken through 5A-5A of FIG. 5;

FIG. 5B is a cross-sectional view of the body of the surgical clip applier of FIGS. 1-5A, as taken through 5B-5B of FIG. 5A;

FIG. 12 is an exploded view of a distal end of a first tubular portion of the shaft assembly of the surgical clip applier as indicated by the detail of FIG. 6;

FIG. 12A is an enlarged perspective view of a first gear of the shaft assembly of the surgical clip applier as indicated by the detail of FIG. 12;

FIG. 12B is an enlarged perspective view of a second gear of the shaft assembly of the surgical clip applier as indicated by the detail of FIG. 12;

FIG. 12C is an enlarged perspective view of a third gear of the shaft assembly of the surgical clip applier as indicated by the detail of FIG. 12;

FIG. 17 is a further longitudinal cross-sectional view of the distal end of a first tubular portion of the shaft assembly of the surgical clip applier as indicated by the detail of FIG. 6, showing the connection between the rack, the first gear, the second gear, the third gear, and the articulation knuckle of the second tubular portion in an articulated position;

FIG. 18 is an enlarged longitudinal cross-sectional view of the indicated area of detail of FIG. 17, illustrating the distal end of a first tubular portion and the second tubular portion in an articulated position;

FIG. 25 is an enlarged cross-sectional view of the indicated area of detail of FIG. 24 of the proximal portion of the second tubular portion as illustrated in FIG. 24;

FIG. 26 is an enlarged cross-sectional view of the indicated area of detail of FIG. 25 illustrating a distal end of a clip pusher of the second tubular portion;

FIG. 41 is an enlarged detail view of the clip carrier and clip pusher as indicated in FIG. 40;

FIG. 42 is a perspective view of the housing of FIG. 40 with the addition of a clip stack thereon;

FIG. 43 is an enlarged detail view of the clip stack as indicated in FIG. 40;

FIG. 46 is an longitudinal cross-sectional view of the clip cartridge, illustrating a complete advancement of the clip pusher during the first stage of operation;

FIG. 47 is an enlarged longitudinal cross-sectional view of the clip cartridge as indicated in FIG. 46, illustrating a return of the clip pusher during a second stage of operation;

FIG. 49 is a perspective view of the jaw structure and the camming plate during the first and second stages of operation, illustrating a separator forcing the jaws apart;

FIG. 50 is a top plan view of the jaw structure and the camming plate during the first and second stages of operation, illustrating the separator forcing the jaws apart;

FIG. 51 is a top plan view of the jaw structure and the camming plate during the third stage of operation, illustrating the formation of the loaded clip about a vessel; and FIG. 52 is a perspective view of the clip formed about and sealing a vessel.

Figure 1:
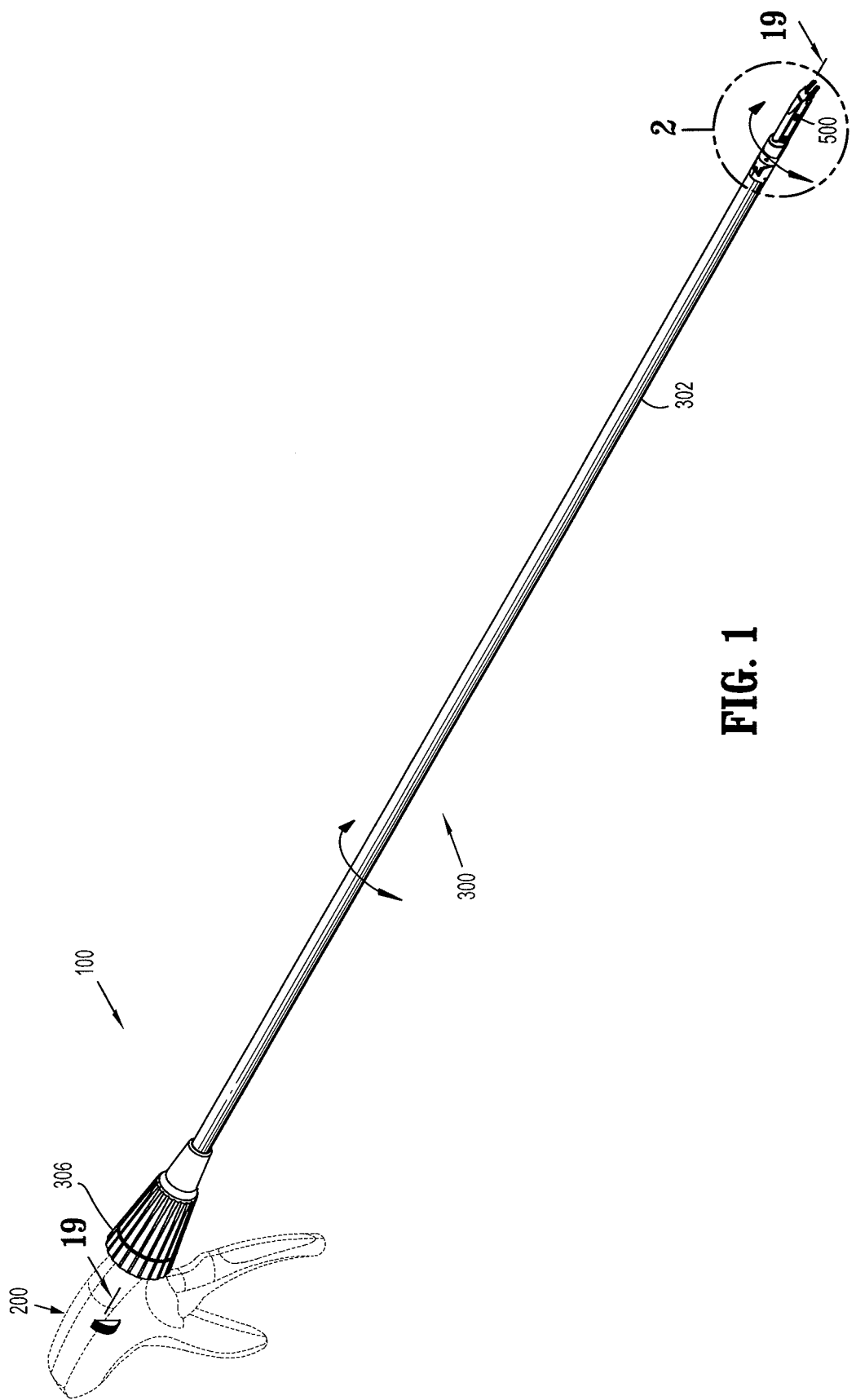
FIG. 1 is a front, perspective view of a surgical clip applier according to an embodiment of the present disclosure.
Figure 2:
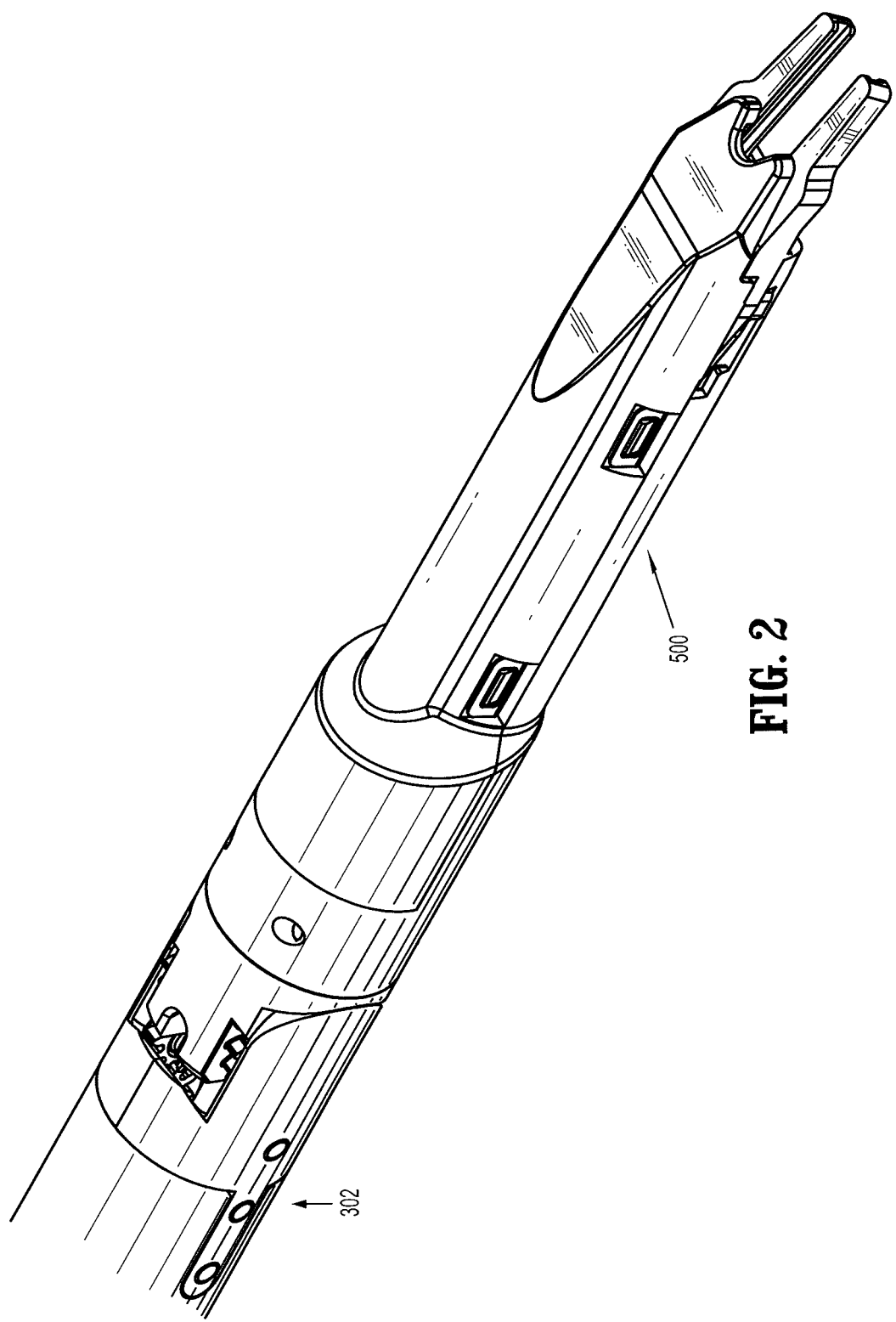
FIG. 2 is a front, perspective view of the indicated area of detail of FIG. 1, illustrating a clip cartridge of the clip applier of FIG. 1.
Figure 3:
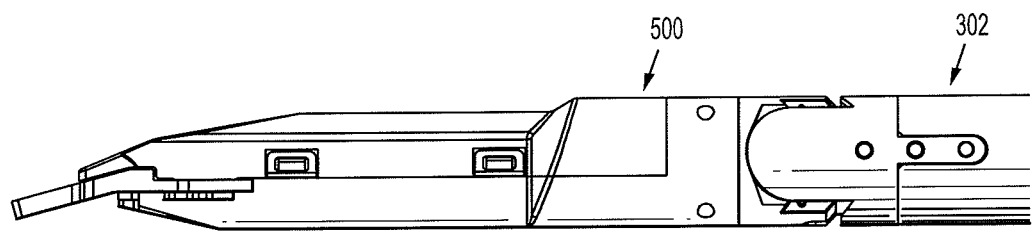
FIG. 3 is a left-side, elevational view of the clip cartridge of the surgical clip applier of FIGS. 1 and 2.

Other features of the present disclosure will become apparent from the following detailed description, taken in conjunction with the accompanying drawings, which illustrate, by way of example, the principles of the present disclosure.

DETAILED DESCRIPTION OF EMBODIMENTS

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal"

refers to the end of the apparatus which is closer to the user and the term "distal" refers to the end of the apparatus which is further away from the user.

With reference to FIG. 1, reference numeral 100 designates an embodiment of the presently disclosed surgical clip applier. In the interest of brevity, the present disclosure focuses on an articulation mechanism and a clip applying end mechanism of surgical clip applier 100. U.S. Pat. No. 7,637,917, filed on Oct. 7, 2005, describes in detail the structure and operation of a surgical clip applier that may incorporate the presently disclosed articulation mechanism and a clip applying end mechanism, the entire content of which is incorporated herein by reference.

Clip applier 100 includes a handle assembly 200 and an articulating endoscopic portion or a shaft assembly 300 extending distally from handle assembly 200. Referring now to FIGS. 5, 5A, 5B-8, handle assembly 200 of surgical clip applier 100 is shown. Handle assembly 200 includes a housing 202 having a first or right side half-section 202a and a second or left side half-section 202b. Handle assembly 200 includes a trigger 208 pivotably supported between right side half-section 202a and left side half-section 202b. Housing 202 of handle assembly 200 may be formed of a suitable plastic material.

As seen in FIGS. 1-15, the shaft assembly 300 includes a first tubular member 302 and a second tubular member or an end effector 500. The first tubular member 302 defines a first longitudinal 'X1' axis and the end effector 500 defines a second longitudinal 'X2' axis. The end effector 500 is located distally from the first tubular member 302. The first tubular member 302 and the end effector 500 are pivotally connected to each other through a common pivot 'Z' axis. The common pivot 'Z' axis is substantially perpendicular to both the first longitudinal 'X1' axis and the second longitudinal 'X2' axis. Shaft assembly 300 and the components thereof may be formed of suitable biocompatible materials, such as, for example, stainless steel, titanium, plastics, and the like.

Figure 5:
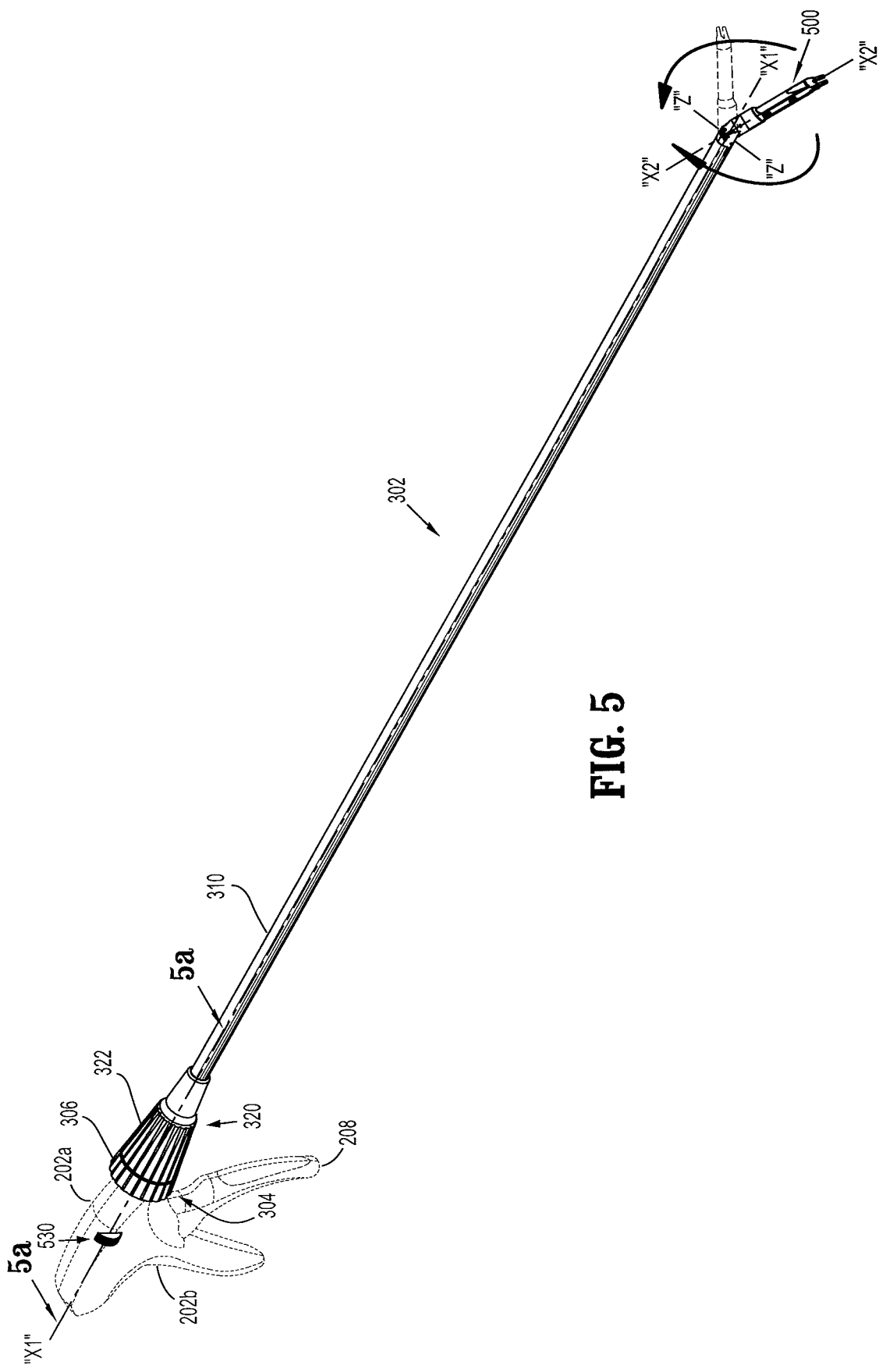
FIG. 5 is a perspective view of the surgical clip applier of FIGS. 1-4 illustrating an articulation of the clip cartridge.

As seen in FIG. 5, the first tubular member 302 has a rotation mechanism 304, and an articulation mechanism 320. The rotation mechanism 304 allows the first tubular member 302 to rotate, with respect to housing 202, about the first longitudinal 'X1' axis. The rotation mechanism 304 includes a rotation knob 306 that is rotatably coupled to the housing 202 and an outer tube 310. The rotation knob 306 is supported between the housing half-sections 202a, 202b.

Figure 6:
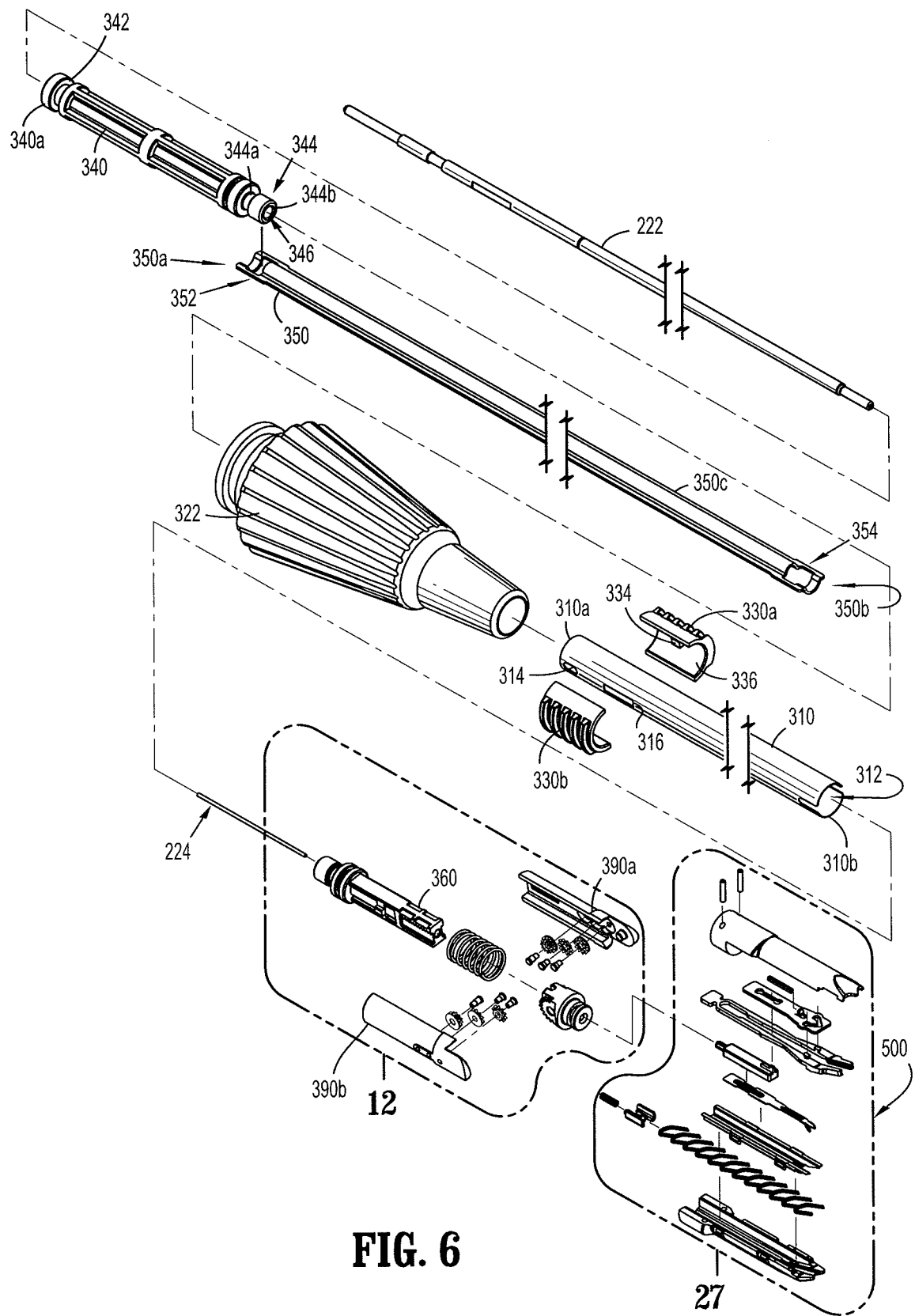
FIG. 6 is an exploded view of a shaft assembly of the surgical clip applier of FIG. 5.
Figure 20:
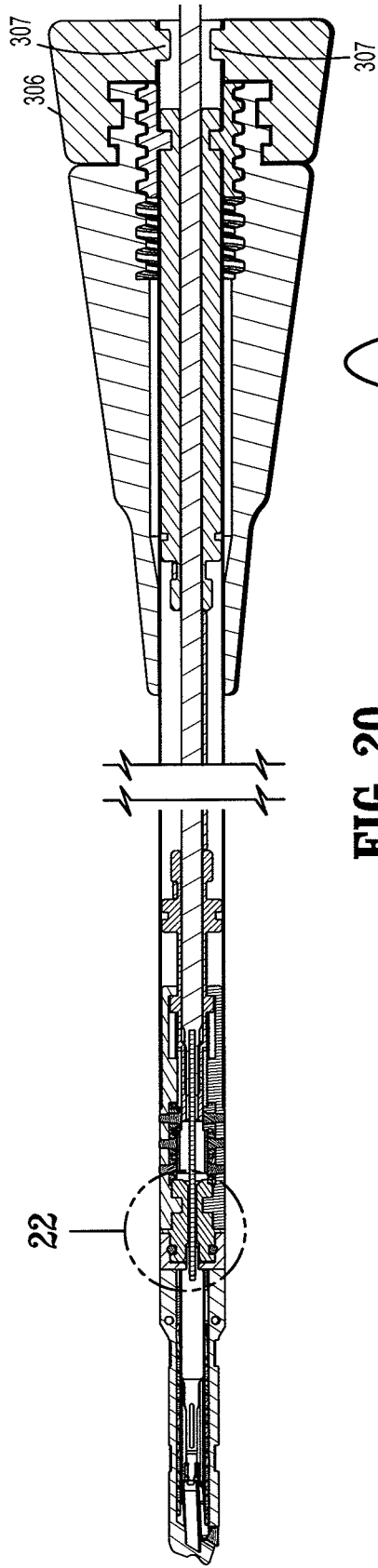
FIG. 20 is an enlarged longitudinal cross-sectional view of the indicated area of detail of FIG. 19 of the shaft assembly.
Figure 21:
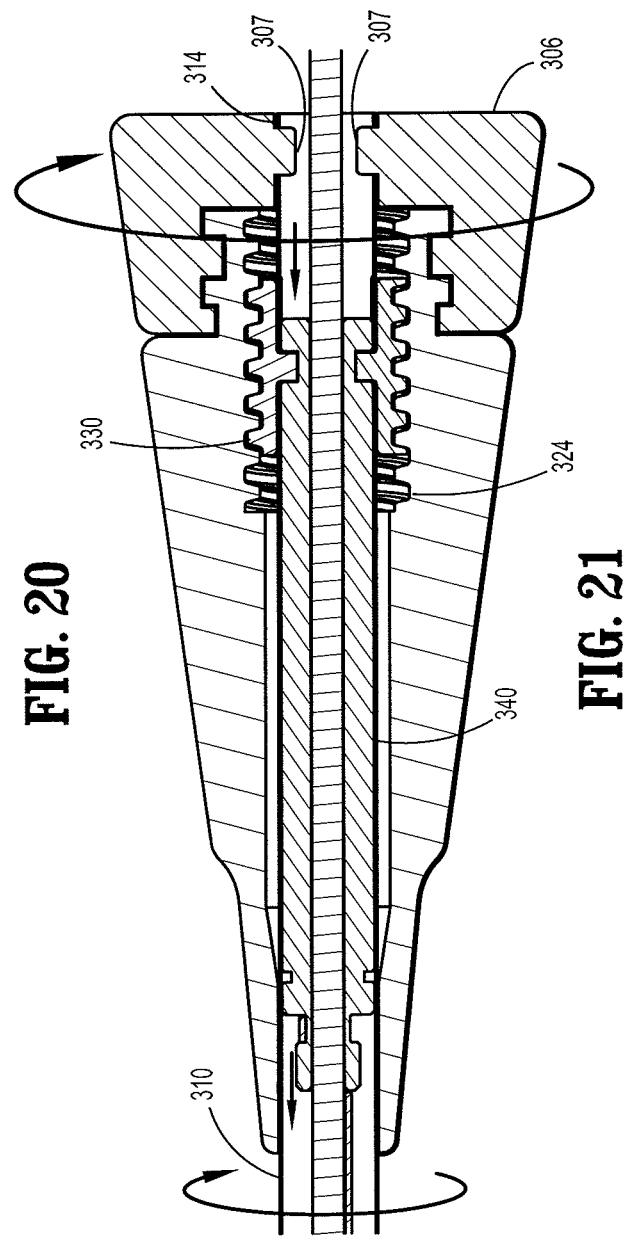
FIG. 21 is an enlarged cross-sectional view of the proximal portion of the shaft assembly as illustrated in FIG. 20.

As seen in FIGS. 5 and 6, the outer tube 310 is at least partially supported by rotation knob 306, and has a proximal end 310a and a distal end 310b. The outer tube 310 defines a lumen 312, extending longitudinally therethrough, and a pair of openings 314, formed near the proximal end 310a of the outer tube 310. With reference to FIGS. 20 and 21, the rotation knob 306 has a pair of nubs 307 that extend into and interface with the openings 314 of the outer tube 310. In use, as seen in FIG. 1, rotation of the rotation knob 306 causes the outer tube 310 to rotate about the first longitudinal 'X1' axis and thus results in the rotation of the entire shaft assembly 300.

As seen in FIG. 5A, clip applier 100 includes a drive assembly 220 operatively connected to trigger 208. The drive assembly 220 is at least partially positioned within the housing 202 of handle assembly 200 and extends through the first tubular member 302 and at least partially into the end effector 500. The drive assembly 220 is able to transfer both a translational force and a rotational force into the end effector 500.

The trigger 208 is operatively connected to a link 210. Link 210 may be connected to an electrical motor 212, which is connected with a drive member 226. The drive member 226 is rotatably attached to the proximal end 222a of the drive rod 222 via a coupling 230 that allows the drive rod 222 to rotate with respect to the drive member 226.

The drive rod 222 may have a cylindrical shape and may extend at least partially along the first tubular member 302. With additional reference to FIG. 44, drive assembly 220 includes a flexible drive cable 224 mounted to the distal end 222b of the drive rod 222. Drive cable 224 extends distally from drive rod 222 and into the end effector 500. It is envisioned that the drive cable 224 may have a cross-sectional shape that is non-circular.

As seen in FIGS. 5-5B, clip applier 100 further includes a positioning mechanism 530. The positioning mechanism 530 is operatively connected with the drive assembly 220 to provide a rotational force to a distal portion or clip cartridge 550 of the end effector 500. As seen in FIG. 5A, the positioning mechanism 530 includes a rotation knob 306, portions of the drive rod 222, and portions of the drive cable 224.

The drive rod 222 includes a contoured outer surface or shaped band 232 that is complimentary to an aperture 242 defined in a mounting member 240 that supports drive rod 222. The aperture 242 is sized slightly larger than the shaped band 232 of the drive rod 222. The over sized aperture 242 allows for longitudinal movement of the drive rod 222 through the aperture 242. The drive rod 222 is able to freely rotate within the first tubular member 302, which allows the drive rod 222 to receive and transmit a rotational force from the rotation knob 306 to the proximal portion of the drive assembly 220.

As seen in FIG. 5, clip applier 100 includes an articulation mechanism 320 operatively connecting the first tubular member 302 with the end effector 500. The articulation mechanism 320 provides a pivot force to the end effector 500 to pivot the end effector 500 about the pivot axis at an angle of up to about 90° relative to the first longitudinal 'X1' axis.

Figure 7:
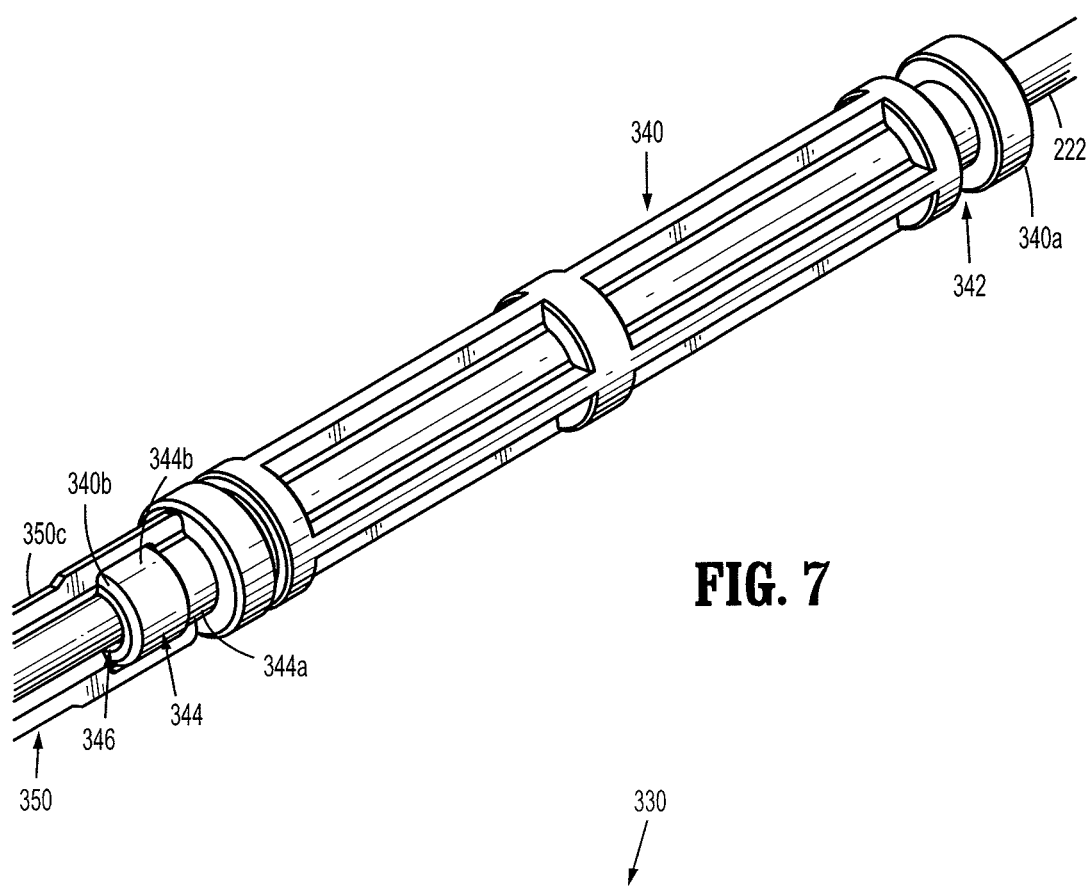
FIG. 7 is an enlarged perspective view of an articulation plunger of the shaft assembly of FIG. 6.
Figure 8:
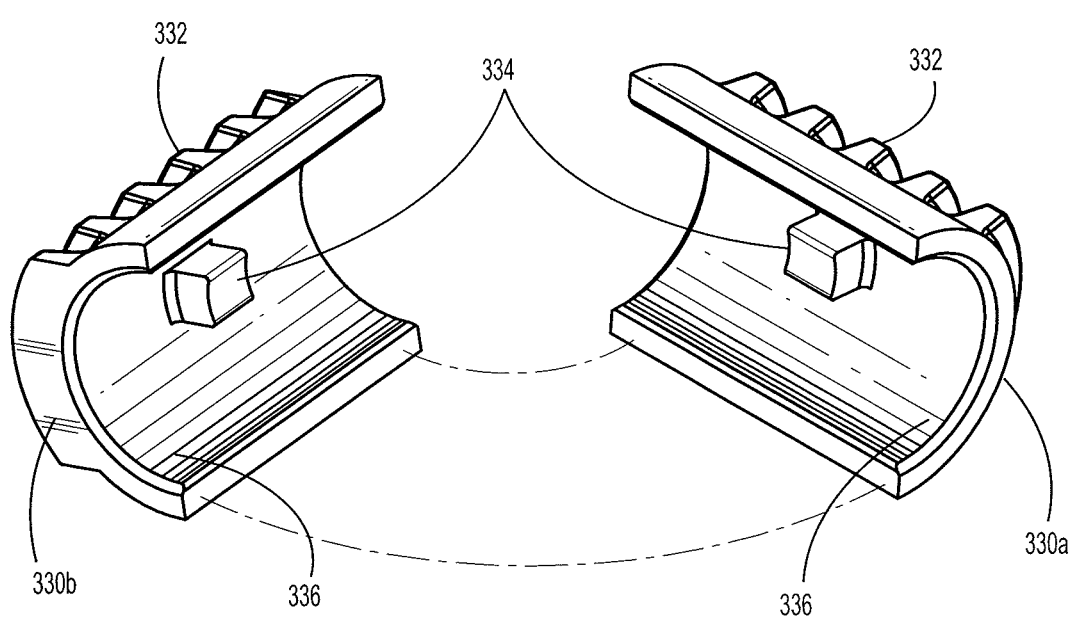
FIG. 8 is an enlarged exploded view of an articulation screw of the shaft assembly of FIG. 6.
Figure 9:
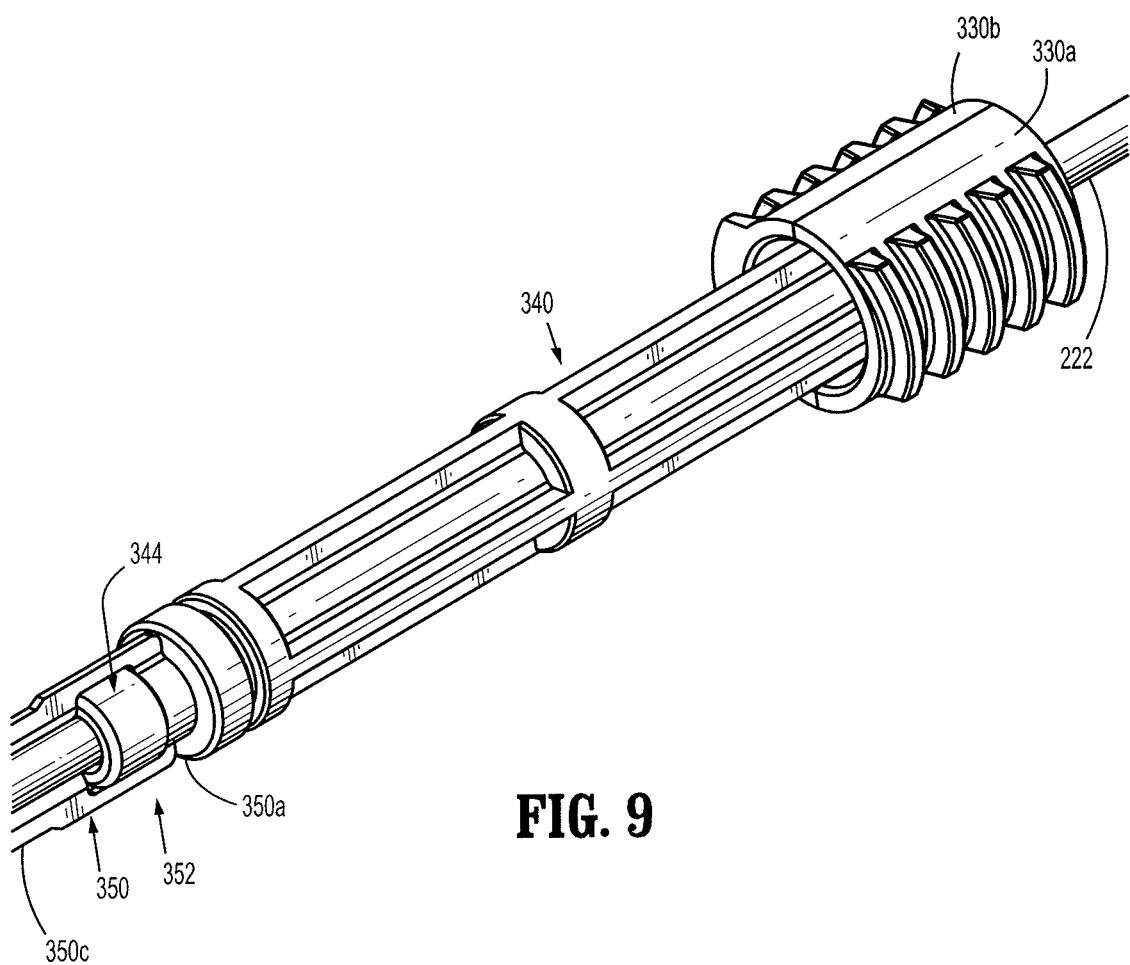
FIG. 9 is an enlarged view of the articulation screw placed about the proximal end of the articulation plunger of the shaft assembly of FIG. 6.

As seen in FIGS. 6 and 12-18, articulation assembly 320 includes an articulation knob 322 rotatably supported by and projecting distally from the rotation knob 306 (FIG. 5A). With reference to FIG. 21, articulation knob 322 has an internal thread 324 that is sized to accept and compliment an external thread 332 (FIG. 8) of an articulation screw 330. As seen in FIG. 8, articulation screw 330 includes a first or right hand half section 330a and a second or left hand section 330b. Each section 330a, 330b has a nub 334 projecting radially inward from an inner curved surface 336. Each nub 334 extends through a slot 316 (FIG. 6) defined in the outer tube 310 and into a radial recess 342 of an articulation plunger 340 (FIG. 7).

Articulation assembly 320 includes an articulation plunger 340 that extends between a proximal end 340a, located proximally of nubs 334 of articulation screw 330 and outer tube 310. Articulation plunger 340 defines a lumen 346 sized to allow passage of the drive rod 222 therethrough. The articulation plunger 340 terminates in a distal end 340b having a mushroom shaped head 344. The mushroom shaped head 344 has a larger distal portion 344b than proximal portion 344a.

Figure 4:
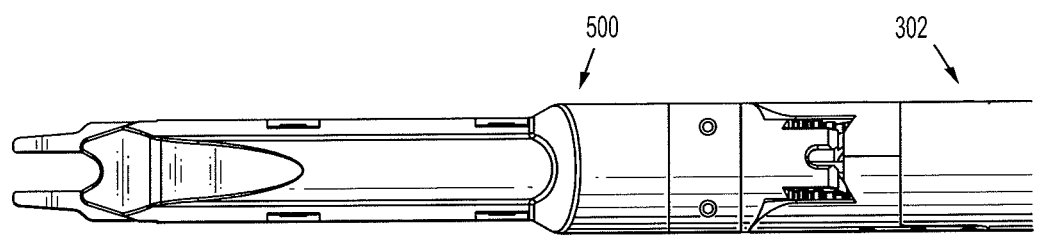
FIG. 4 is a top, plan view of the clip cartridge of the surgical clip applier of FIGS. 1-3.

With reference to FIGS. 6-7 and 9-11, clip applier 100 includes a shaft 350 defining a proximal portion 352 having a proximal end 350a, a distal portion 354 having a distal end 350b, and a center portion 350c. The shaft 350 is semi-cylindrical in shape to allow the drive rod 222 to pass therealong, and extends longitudinally within the outer tube 310. As shown in FIG. 4, the proximal end 350a and the distal end 350b of shaft 350 are curved in an opposite transverse direction than the center portion 350c. Shaft 350 defines a distal aperture that separates the distal portion 354 from the center portion 350c and a proximal aperture that separates the proximal portion 352 from the center portion 350c. The distal aperture of shaft 350 is sized and configured to accept the distal portion 334b of head 344 of the articulation plunger 340 therein and the distal portion forms an arc that is sized and configured to loosely set about distal portion 344b of head 344 of the articulation plunger 340.

Figure 11:
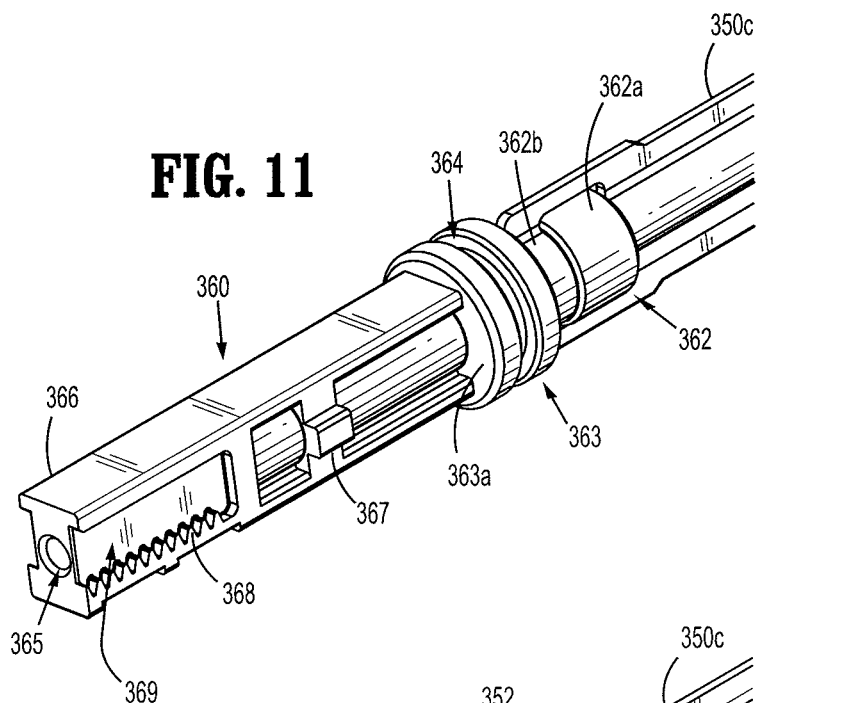
FIG. 11 is an enlarged perspective view of a rack coupled to the shaft of the shaft assembly of FIG. 6.
Figure 10:
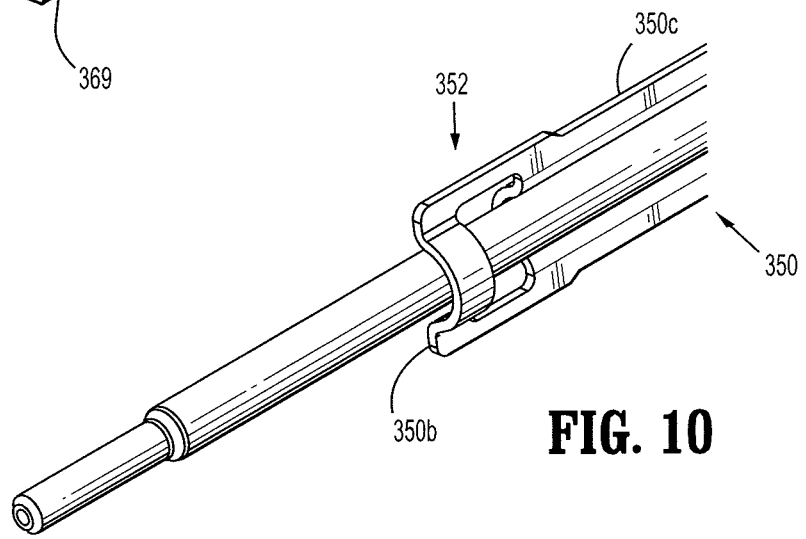
FIG. 10 is an enlarged perspective view of a distal portion of a shaft of the shaft assembly of FIG. 6, with the drive shaft extending therethrough.
Figure 13:
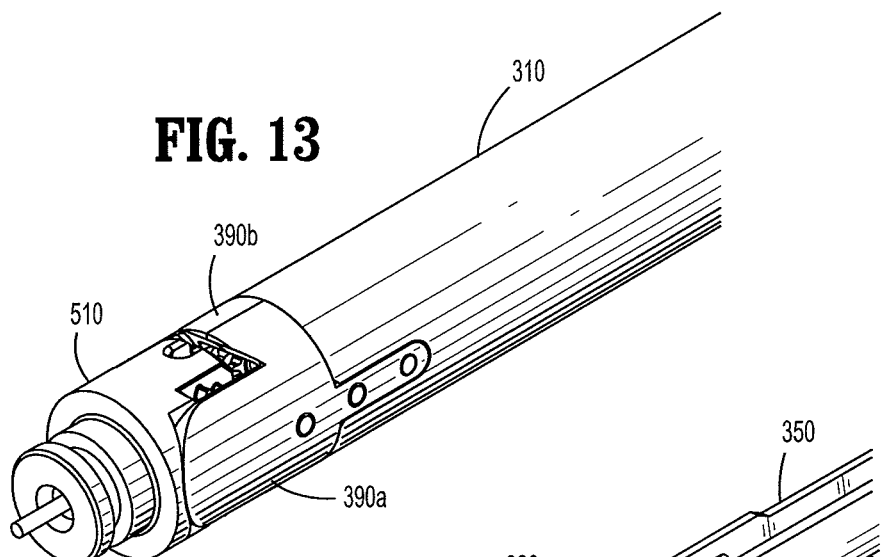
FIG. 13 is a front, perspective view of the distal end of a first tubular portion of the shaft assembly of the surgical clip applier as indicated by the detail of FIG. 6.

As seen in FIG. 11, the proximal portion 352 of the shaft 350 removably couples the shaft 350 to a rack 360. A proximal end 362a of the rack 360 is formed in a mushroom shaped tail 362. The proximal end 362a of the mushroom shaped tail 362 is larger than the distal end 362b of the mushroom shaped tail 362. The proximal aperture of the shaft 350 is sized to accept the proximal end 362b of the mushroom shaped tail 362 therein. The proximal portion 352 of shaft 350 forms an arc that is sized to set loosely about distal end 362b of the mushroom shaped tail 362 of the rack 360.

As seen in FIG. 11, rack 360 includes a cylindrical section 363 and a proximal end 362b disposed immediately adjacent to cylindrical section 363 and that is sized slightly smaller than an inner diameter of the outer tube 310. The cylindrical section 363 may have one or more recesses 364 about the perimeter that are sized to accept an O-seal 382 therein, as shown in FIG. 17. The O-seal 382 is deformable to fill the space between the cylindrical section 363 of the rack 360 and the inner diameter of the outer tube 310 to substantially seal the distal portion of the first tubular member 302.

Figure 14:
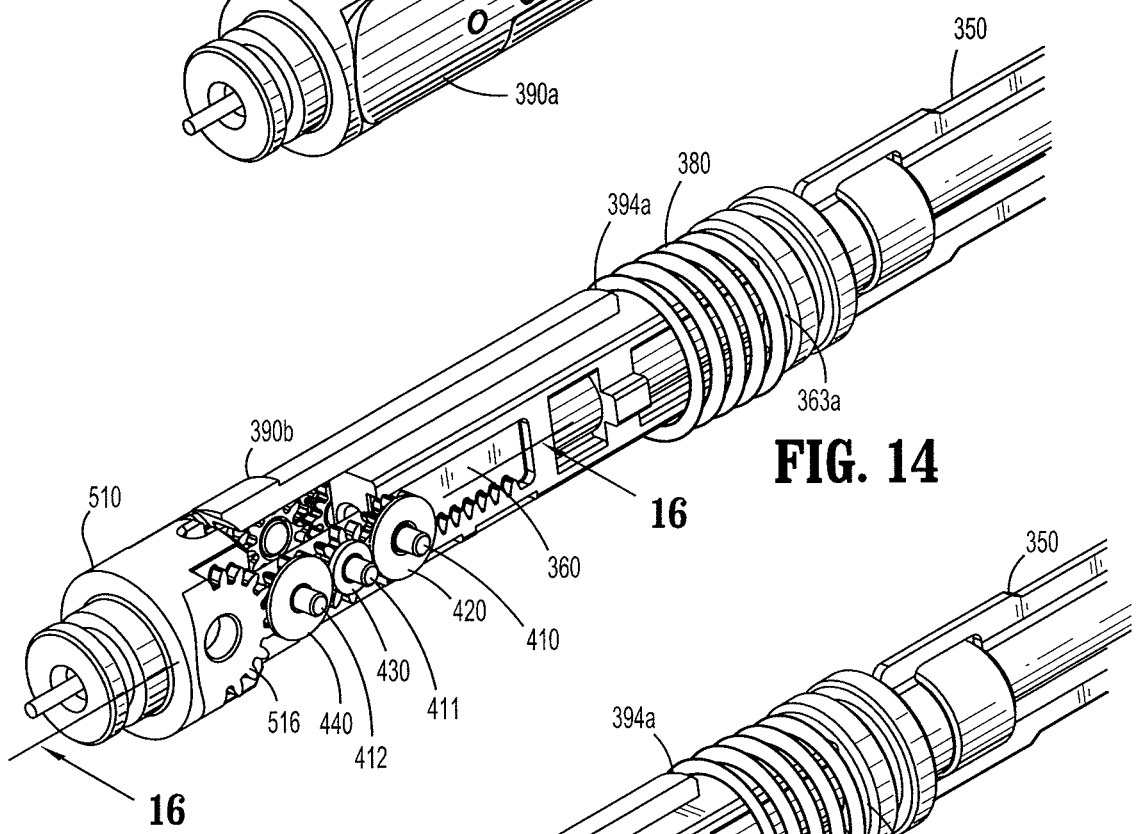
FIG. 14 is a front, perspective view of the distal end of a first tubular portion of the shaft assembly of the surgical clip applier as indicated by the detail of FIG. 6, with a right side end cover and the outer tube removed.

As shown in FIG. 11, the rack 360 defines a central passageway 365 along the first longitudinal 'X1' axis sized to allow passage of the drive cable 226 therethrough. A distal portion 366 of the rack 360 has a rectangular cross-sectional shape. With reference to FIGS. 12 and 14, the distal portion 366 is sized to fit through the longitudinal center of a helical spring 380. The spring 380 has an outer diameter sized to be slightly smaller than the cylindrical section 363 of the rack 360. As a result, the spring is prevented from passing proximally beyond the cylindrical section 363 of the rack 360.

As shown in FIGS. 11 and 12, the distal portion 366 of rack 360 includes at least two protrusions 367 and a set of longitudinally aligned linear teeth 368. The two protrusions 367 extend outward in opposite directions from the proximal portion 366 and are aligned and sized to be placed into slots 391 defined in an inner surface 392 of an end cover 390. As seen in FIG. 12, the end cover 390 has a right hand side cover 390a and a left hand side cover 390b. The outer proximal portion 393 of end cover 390 defines an outer diameter that is sized to enable the end cover 390 to be pressed into the distal end 310b of the outer tube 310 and establish an interference fit between the end cover 390 and the outer tube 310.

Figure 15:
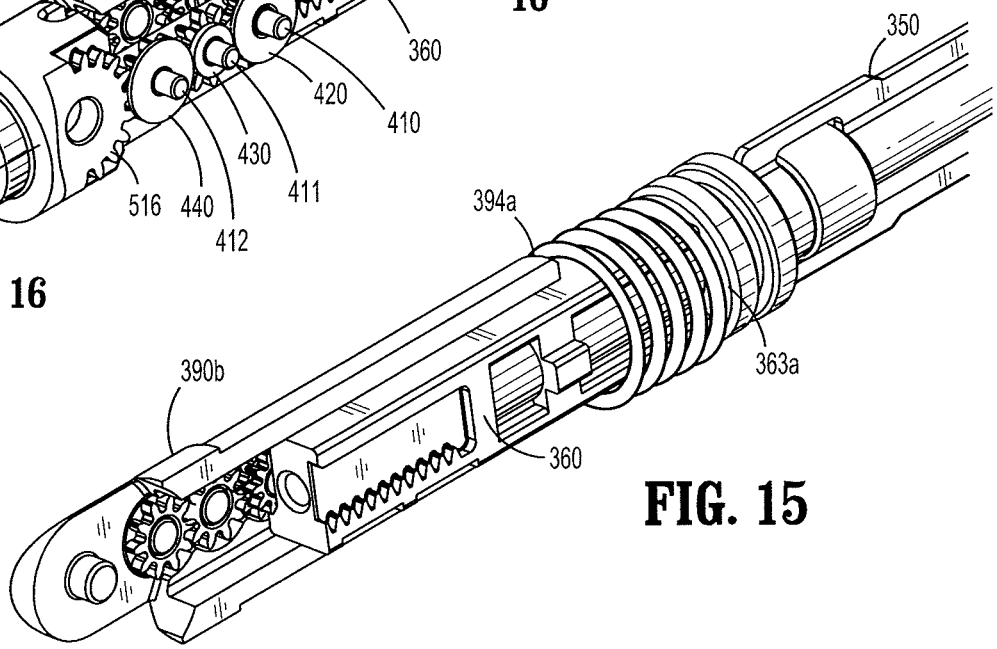
FIG. 15 is a front, perspective view of the distal end of a first tubular portion of the shaft assembly of the surgical clip applier as indicated by the detail of FIG. 6, with a right side end cover, the outer tube, the first gear, the second gear, and the third gear removed.

The inner surface 392 of the end cover 390 has a rectangular shape that is sized to be slightly larger than the rectangular cross-section of the rack 360 to allow at least partial longitudinal movement of the rack 360 therein. A proximal end 394a of the end cover 390 is sized to be smaller than the spring 380 to provide a biasing surface for the spring 380. As seen in FIGS. 14 and 15, the spring 380 is interposed between a distal surface 363a of the cylindrical portion 363 and the proximal end 394a of the end cover 390 to bias the rack 360 proximally.

Figure 16:
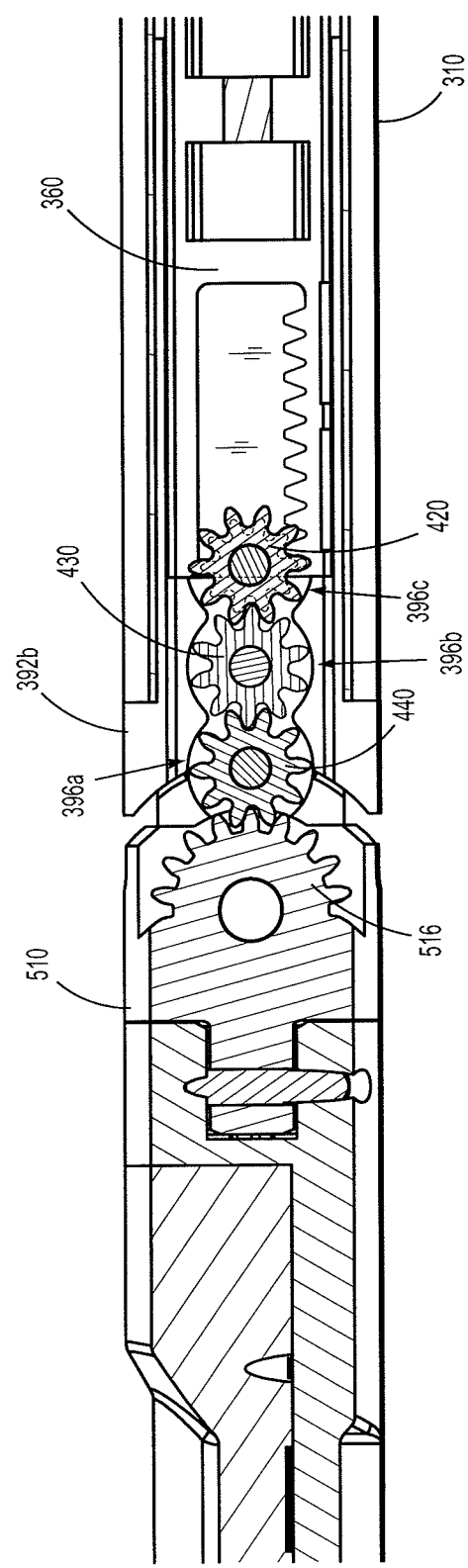
FIG. 16 is a longitudinal cross-sectional view of the distal end of a first tubular portion of the shaft assembly of the surgical clip applier as indicated by the detail of FIG. 6, showing the connection between the rack, the first gear, the second gear, the third gear, and a articulation knuckle of the second tubular portion.
Figure 19:
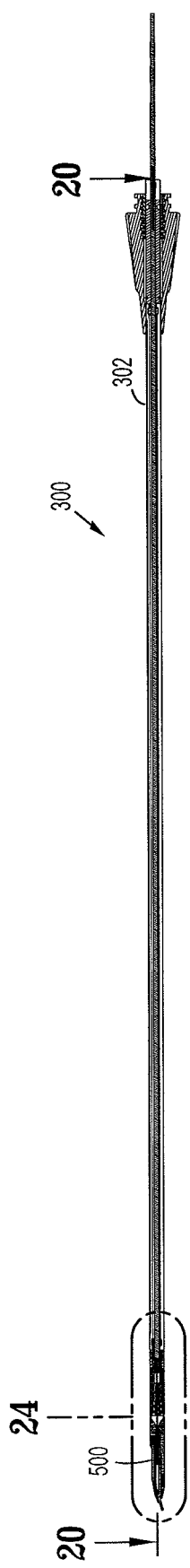
FIG. 19 is a longitudinal cross-sectional view of the shaft assembly of FIG. 6, as taken through 19-19 of FIG. 1.

As seen in FIGS. 12 and 16, the inner surface 392 of the end cover sections 390a, 390b define a series of three circular recesses 396a, 396b, and 396c. Each of the three circular recesses 396a, 396b, and 396c are centered about an aperture 397a, 397b, and 397c through each of the end cover sections 392a, 392b.

As stated above, the rack 360 is located within the outer tube 310 and extends into the end cover 390. The rack 360 is configured to reciprocate along the first longitudinal 'X1' axis. A proximal position and a distal position of the rack 360 is defined by the two protrusions 367 that are located within respective slots 391 of end cover 390. The two protrusions 367 of rack 360, acting against the proximal end 391a of the slots 391, define the proximal-most position of the rack 360. The two protrusions 367 of rack 360, acting against the distal end 391b of the slots 391, define the distal-most position of the rack 360.

While rack 360 includes a pair of opposed longitudinally arranged teeth 368 that engage respective gear sets and mating structure, only a single set of teeth 368 of rack 360 and a single respective gear set and mating structure will be described herein for the purpose of clarity. As shown in FIGS. 12-18, rack 360 has a pair of longitudinally arranged teeth 368 on opposing sides of the distal portion 366. The longitudinally arranged teeth 368 are defined by recesses 369 in the distal portion 366 that form the distal portion 366 into an "I" beam, wherein the longitudinally arranged teeth 368 are formed along an inside of flanges of the "I" beam that extend in opposing directions. The longitudinally arranged teeth 368 are in intimate contact with a first gear 420 supported in end cover 390.

As seen in FIG. 12A, the first gear 420 defines a center aperture 421, a circular base 422, a first circular set of teeth 423, and a second circular set of teeth 424. The first circular set of teeth 423 is smaller in diameter than and stacked upon the second set of teeth 424. The circular base 422 forms a substantially similar outer diameter as the second set of teeth 424. As seen in FIG. 12, a first pin 410 has a head portion 410a that is larger than the aperture 421 of first gear 420, a body portion 410b slightly smaller in diameter than the center aperture 421, and a tail portion 410c that is sized to allow the first pin 410 to be press fit into the aperture 397a in the cover 390. An interference fit between the tail portion 410c and the cover 390 retains the tail portion 410c in the aperture 397a and holds the first gear 420 at least partially within the first recess 396a of the end cover 390. The longitudinally arranged teeth 368 of the rack 360 and the first gear 420 are connected, such that longitudinal movement of the rack 360 relative to first gear 420 results in a rotational movement in a first direction of the first gear 420.

The first gear 420 is operatively connected with a second gear 430 of the gear set. As seen in FIG. 12B, the second gear 430 defines a center aperture 431, a raised base 432, and a circular set of teeth 433. The raised base 432 is circular in cross-sectional shape and has a substantially smaller outer diameter than the circular set of teeth 423. A second pin 411 has a head portion 411a that is larger than the aperture 431, a body portion 411b that is slightly smaller in diameter than the center aperture 431, and a tail portion 411c that is sized to allow the second pin 411 to be press fit into the aperture 397b in the cover 390. An interference fit between the tail portion 411c and the cover 390 retains the tail portion 411c in the aperture 397b and holds the second gear 430 at least partially within the second recess 396b of the end cover 390. The second circular set of teeth 424 of the first gear 420 is interconnected with the circular set of teeth 433 of the second gear 430, such that rotational movement of the first gear 420 in a first direction results in a rotational movement of the second gear 430 in a second direction.

The second gear 430 is operatively connected with a third gear 440 of the gear set. As seen in FIG. 12c, the third gear 440 defines a center aperture 441, a circular base 442, and a circular set of teeth 443. The circular base 442 forms a substantially similar outer diameter as the circular set of teeth 443. The circular base 442 is substantially equal in height as both the raised base 432 of the second gear 430 and the circular base 422 of the first gear 420. A third pin 412 has a head portion 412a that is larger than the aperture 441, a body portion 412b that is slightly smaller in diameter than the center aperture 441, and a tail portion 412c that is sized to allow the third pin 412 to be press fit into the aperture 397c in the cover 390. An interference fit between the tail portion 412c and the cover 390 retains the tail portion 412c in the aperture 397c and holds the third gear 440 at least partially within the second recess 396c of the end cover 390. The circular set of teeth 433 of the second gear 40 is interconnected with the circular set of teeth 444 of the third gear 440, such that rotational movement of the second gear 430 in the second direction results in a rotational movement of the third gear 440 in the first direction.

Located distally of the third gear 440, each of the end cover sections 392a, 392b defines a boss 398 extending radially inward from the distal portion 395b of the end cover sections 392a, 392b. The bosses 398 capture and secure a cylindrical distal, portion 522 of the end effector 500 to the first tubular member 302.

As seen in FIG. 12, cylindrical distal portion 522 of the end effector 500 has a knuckle 510. The knuckle 510 includes a bifurcated proximal portion 514 and a cylindrical distal portion 522. The bifurcated proximal portion 514 defines a pivoting aperture 511 that is perpendicular to both the first longitudinal 'X1' axis and the second longitudinal 'X2' axis. The pivoting aperture 511 defines the pivot 'Z' axis. The pivoting aperture 511 is circular in cross-sectional shape and is sized to accept the bosses 398 therein. The size and alignment of the bosses 398 allow the end cover sections 392a, 392b to sandwich the knuckle 510 therebetween. As a result of the circular bosses 398 projecting into the circular pivoting aperture 511, the end effector 510 is able to pivot or swing about the 'Z' axis.

The bifurcated proximal portion 514 of knuckle 510 includes two gear segments 516a, 516b that are integrally formed therewith and that extend proximally about the proximal end 510a of the knuckle 510. Each gear segment 516 defines an arcuate set of teeth 517 that are operatively connected with the third gear 440.

Figure 24:
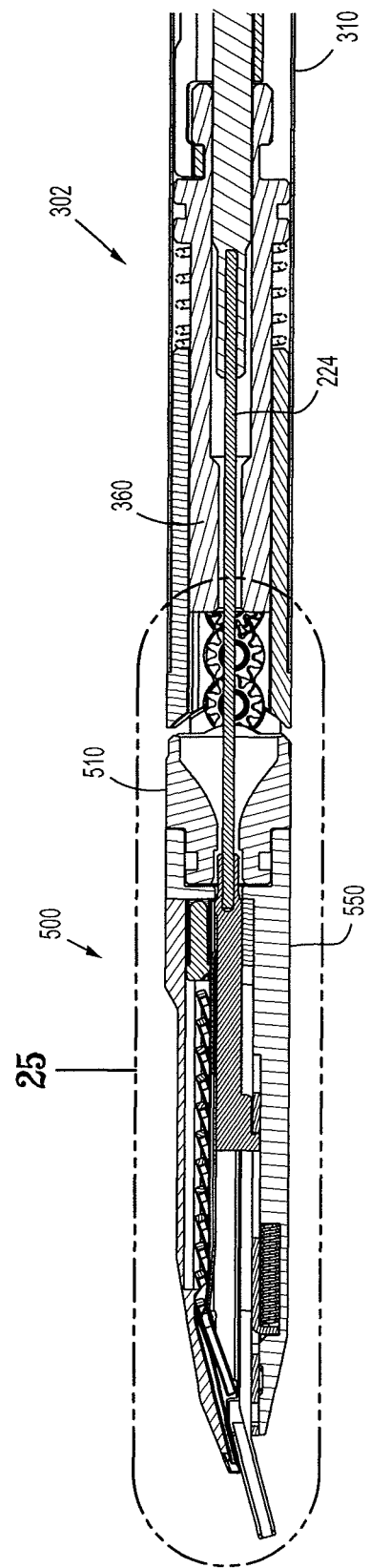
FIG. 24 is an enlarged cross-sectional view of the indicated area of detail of FIG. 19 of the shaft assembly.

The knuckle 510 further defines a lumen 518 through the center thereof, and a circular channel 520 about the cylindrical distal portion 522. The circular channel 520 is located proximally from the distal end 510b of the knuckle 510. The center lumen 518 is sized to allow at least partial passage of the drive cable 224 therethrough and at least partially into a clip cartridge 550 (FIGS. 24 and 27) of the end effector 500.

The operation of the articulation mechanism will now be discussed in reference to FIGS. 6-21. With specific reference to FIGS. 20 and 21, rotation of the articulation knob 322 (FIG. 5) with respect to the rotation knob 306 and the outer tube 310 produces longitudinal movement of the articulation screw 330 by causing the internal thread 324 of the articulation knob 322 to react against the external thread 332 of the articulation screw 330. The articulation screw 330 is rotationally fixed with respect to the outer tube 310 by the nubs 334. As a result, the articulation screw 330 can only move longitudinally as the articulation knob 332 is rotated about the articulation screw 330. Therefore, rotation of the articulation knob 322 in a first direction causes the movement of the articulation screw 330 in distal direction and rotation of the articulation knob 322 in a second direction causes the movement of the articulation screw 330 in proximal direction.

Axial movement of the articulation screw 330 causes the nubs 334 to react against the articulation plunger 340 to cause longitudinal movement of the articulation plunger 340 in the same direction. Movement of the articulation plunger 340 causes longitudinal movement of the shaft 350 and, in turn, longitudinal movement of the rack 360.

As discussed above, the first gear 420 is operatively connected with the linear teeth 368 of the rack 360. With specific reference to FIGS. 17 and 18, as the rack 360 is forced to move proximally, the first gear 420 is rotated in a first direction causing the second gear 430 to be rotated in a second direction. The second gear 430 causes the third gear 440 to be rotated in the same direction as the first gear 420. The third gear 440 reacts against the geared segments 516 causing the second tubular member 302 to pivot about the pivot 'Z' axis.

Figure 22:
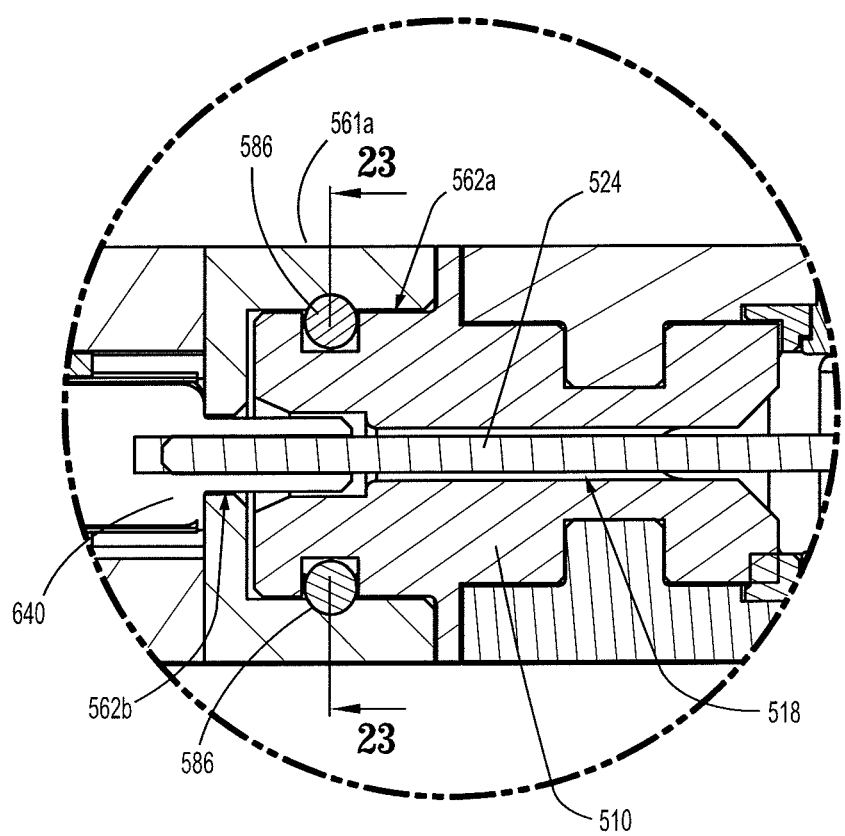
FIG. 22 is an enlarged cross-sectional view of the indicated area of detail of FIG. 20 of the shaft assembly as detailed in FIG. 20.
Figure 23:
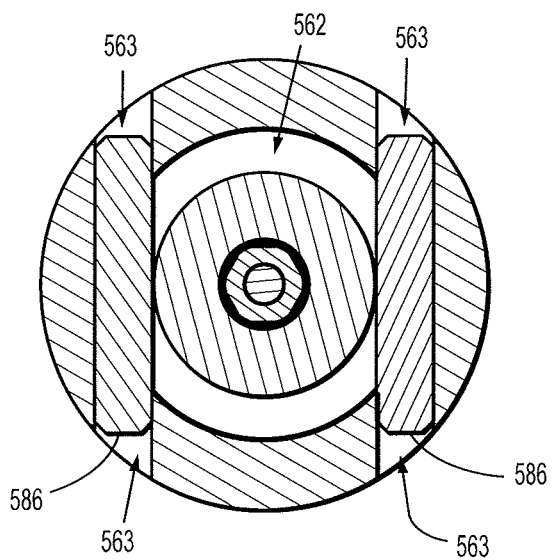
FIG. 23 is an enlarged cross-sectional view of the indicated area of detail of FIG. 22 of the shaft assembly.
Figures 27, 27A:
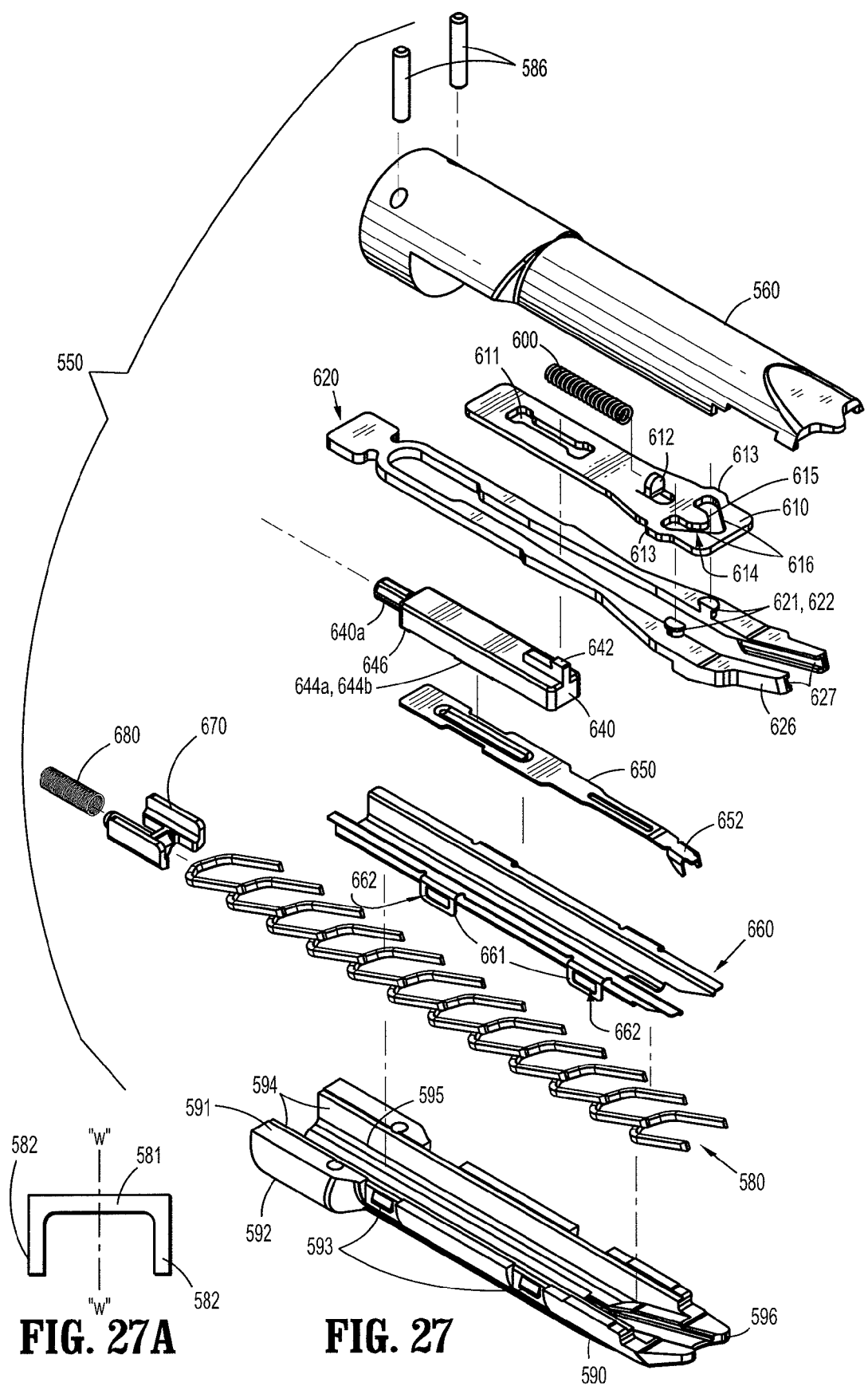
FIG. 27 is a perspective view of the clip cartridge of the second tubular portion as indicated in FIG. 6, with parts separated.
FIG. 27A is a front, plan view of a clip used in the cartridge of the surgical clip applier of FIG. 27.
Figure 28:
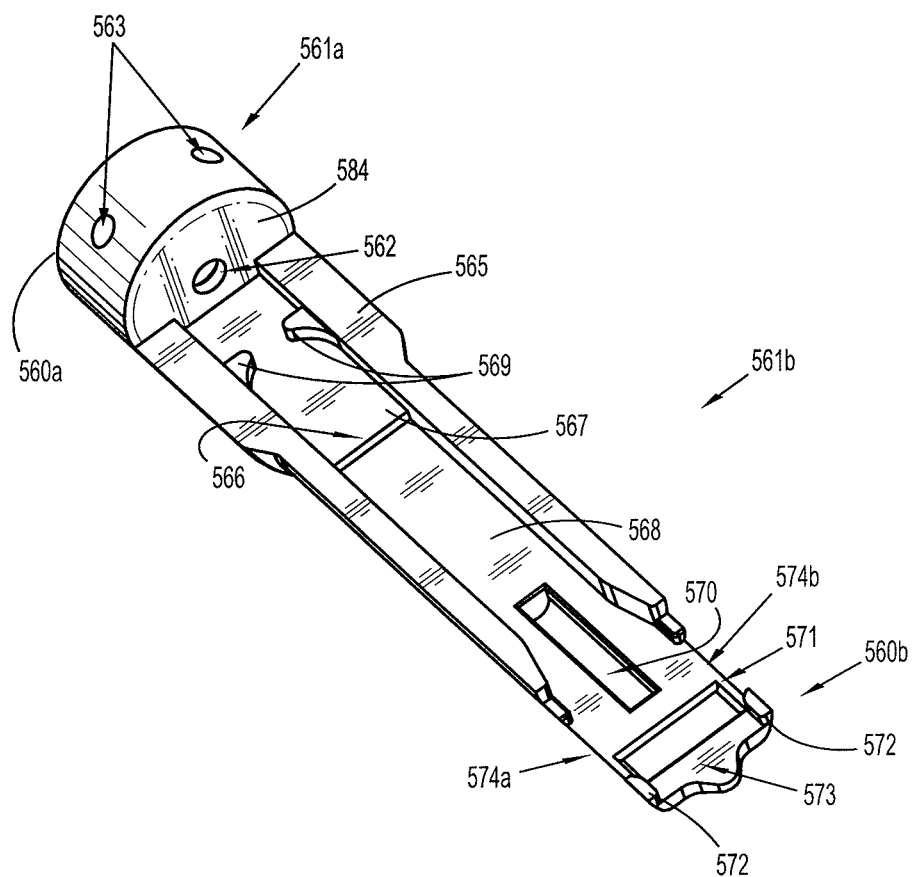
FIG. 28 is a perspective view of a housing of the clip cartridge of FIG. 27.

As seen in FIGS. 1-6, end effector 500 is in the form of a surgical clip applier and is configured to support a clip cartridge 550. As seen in FIG. 27, clip cartridge 550 has a housing or base portion 560 and a cover 590. With reference to FIG. 28, the housing 560 includes a proximal portion 561a and a distal portion 561b. The proximal portion 561a of housing 560 is cylindrical in shape and defines a longitudinal passageway 562 therethrough. The longitudinal passageway 562 is co-axially located with the second longitudinal 'X2' axis and transitions, as seen in FIGS. 22 and 23, from a larger cylindrical portion 562a of the passageway 562, sized to accept the cylindrical distal portion 522 of the knuckle 510, to a narrower or smaller portion 562b that is co-axially located with the center lumen 518 of the knuckle 510.

Now referring to FIGS. 22-23 and 27-28, the proximal portion 561a of the housing 560 also defines a pair of parallel pinholes 563 located distally from the proximal end 560a of the proximal portion 561a. The pair of pinholes 563 are aligned off-center, such that each of the pair of pinholes 563 creates a single passageway through the proximal portion 561a to extend into and through the larger cylindrical portion 562a of the longitudinal passageway 562. Each hole 563 is sized to accept a pin 586 therein to cause a friction or interference fit of the pin 586 within the pinhole 563. Each of the pair of the pinholes 563 is located to position the pins 586 with the circular channel 520 of the knuckle 510. As a result, the clip cartridge 550 is longitudinally restrained to the knuckle 510 by the pins 586, while allowing the clip cartridge 550 to rotate about the knuckle 510.

As seen in FIG. 28, the distal portion 561b of the housing 560 is a semi-cylindrical structure that extends distally from a perpendicular surface 564 of the proximal portion 561a. With reference to FIG. 28, the semi-cylindrical distal portion 561b has a pair of horizontal walls 565 that extend partially along the distal portion 561b, a first recessed surface 567, and a second recessed surface 568 that define a longitudinally extending recess 566 along the distal portion 561b of the housing 560, between the pair of horizontal walls 565. A pair of inward projection locks 569 extend into the longitudinally extending recess 566 along the first recessed surface 567 with one projection lock extending inward from each of the horizontal walls 565. A spring slot 570 is defined longitudinally along the second recessed surface 568 at a location distal of spring slot 570. A horizontal recess 571 is defined radially along the second recessed surface 568 at a location distal of spring slot 570. Two stops 572 project from the second recess surface 568 along the distal end 560b and define a pair of longitudinal openings 574a, 574b between the horizontal walls 565 and the stops 572, and a distal opening 573 between the two stops 572. The distal portion 561b of the housing 560 is shaped and sized to mate with the cover 590.

As shown in FIG. 27, the clip cartridge 550 includes a plurality or series of clips or fasteners 580, a cam spring 600, a cam plate 610, a jaw structure 620, a block member 640, a feed bar 650, a clip carrier 660, a clip follower 670, and a follower spring 680, between the housing 560 and the cover 590.

The plurality of surgical clips 580 are retained within the clip cartridge 550 for application to tissue. As shown in FIG. 27A, each clip 580 has a pair of legs 582a, 582b extending from a backspan 581 and defines a clip axis 'W' extending substantially parallel with the pair of legs 582a, 582b. The clips 580 are located adjacent to one another to form an angled stack. With reference to FIGS. 42 and 43, the series of fasteners or clips 580 are arranged within the clip cartridge 550 to form an angle of between, but not including, 0° and 90° with the second longitudinal 'X2' axis. The series of clips 580 are stacked in or at an angle with respect to the second longitudinal 'X2' axis and extend along in an offset parallel fashion with the second longitudinal 'X2' axis. The shape of the clip 580 may be U-shaped, V-shaped, or some other shape.

As seen in FIGS. 48-51, clip cartridge 550 includes a jaw closure mechanism 532 including the camming plate 610, which is connected with the drive assembly 220 through the block member 640 to provide an approximating force to the jaw structure 620.

Figure 29:
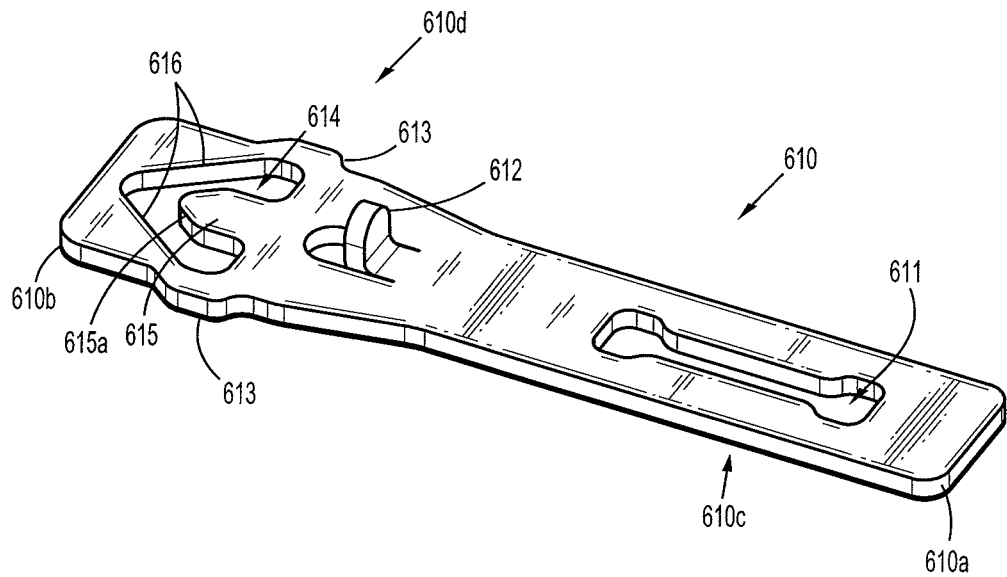
FIG. 29 is a perspective view of a camming plate of the clip cartridge of FIG. 27.

With reference to FIGS. 27 and 29, the cam plate 610 defines a proximal portion 610c and a camming or distal portion 610d. A dog bone shaped aperture 611 is defined in the proximal portion 610c and a camming aperture 614 is defined in the camming portion 610d. The cam plate 610 has a finger 612 that extends perpendicularly to a top/bottom surface thereof and a pair of stops 613 extending outward from the camming portion 610c along a side edge thereof.

The camming aperture 614 is substantially "V" shaped. The "V" shaped camming aperture 614 defines a protrusion or separator 615 extending into the center of the aperture and a pair of camming surfaces 616 along the outer edges of the aperture. With reference to FIGS. 30 and 49-51, the camming aperture 614 mates with a pair of posts 621 that extend vertically from the jaw structure 620. Each post 621 includes a head 622 that acts to secure the cam plate 610 and the jaw structure 620 together to maintain contact between the two components.

Figure 37:
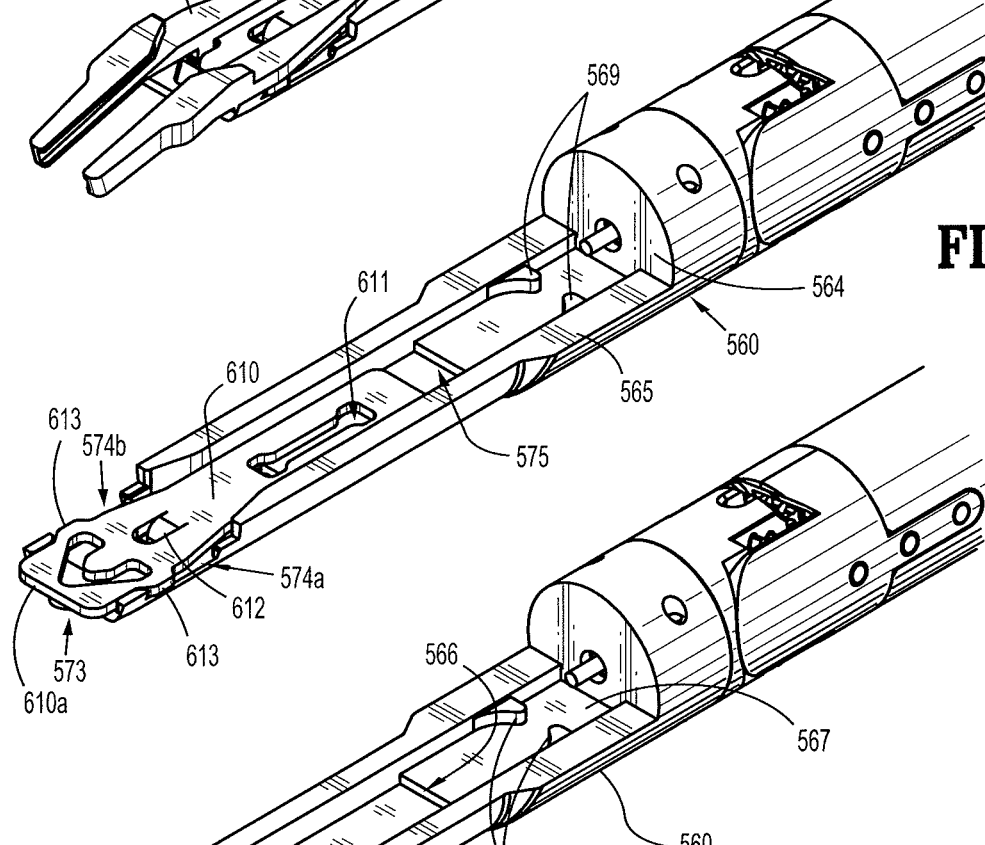
FIG. 37 is a perspective view of the housing of FIG. 36 with the jaw structure removed therefrom.

With reference to FIG. 37, cam plate 610 is located along the second recessed surface 568 of housing 560. The stops 613 of cam plate 610 extend radially outward through the longitudinal openings 574a, 574b of housing 560 to limit longitudinal movement of the cam plate 610 to the length of openings 574a, 574b. The proximal portion 610c of the cam plate 610 is sized to fit into the longitudinal extending recess 566 of the housing 560. When cam plate 610 is at a distal-most position relative to housing 560, a gap 575 is formed between the proximal end 610a of the cam plate 610 and the second recessed surface 567. The finger 612 is sized to be positioned within the spring slot 570 (FIG. 28) of the housing 560. In use, longitudinal movement of the camming plate 610 moves the cam aperture 614 relative to the posts 621 of jaw structure 620.

Figure 38:
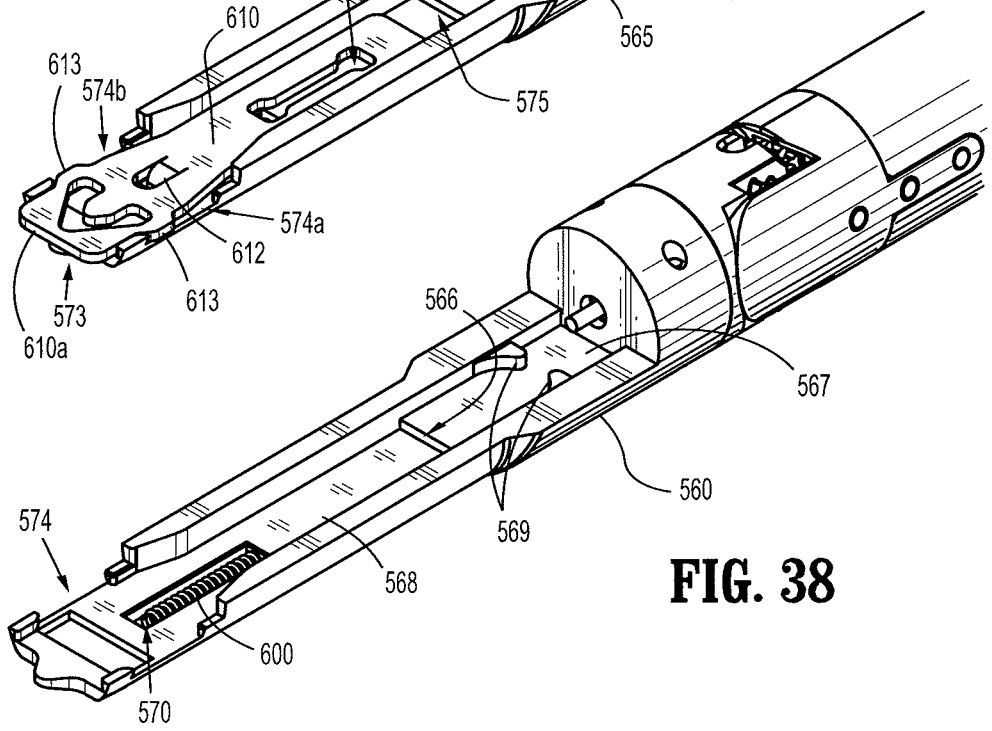
FIG. 38 is a perspective view of the housing of FIG. 36 with the jaw structure and the camming plate removed therefrom.
Figure 39:
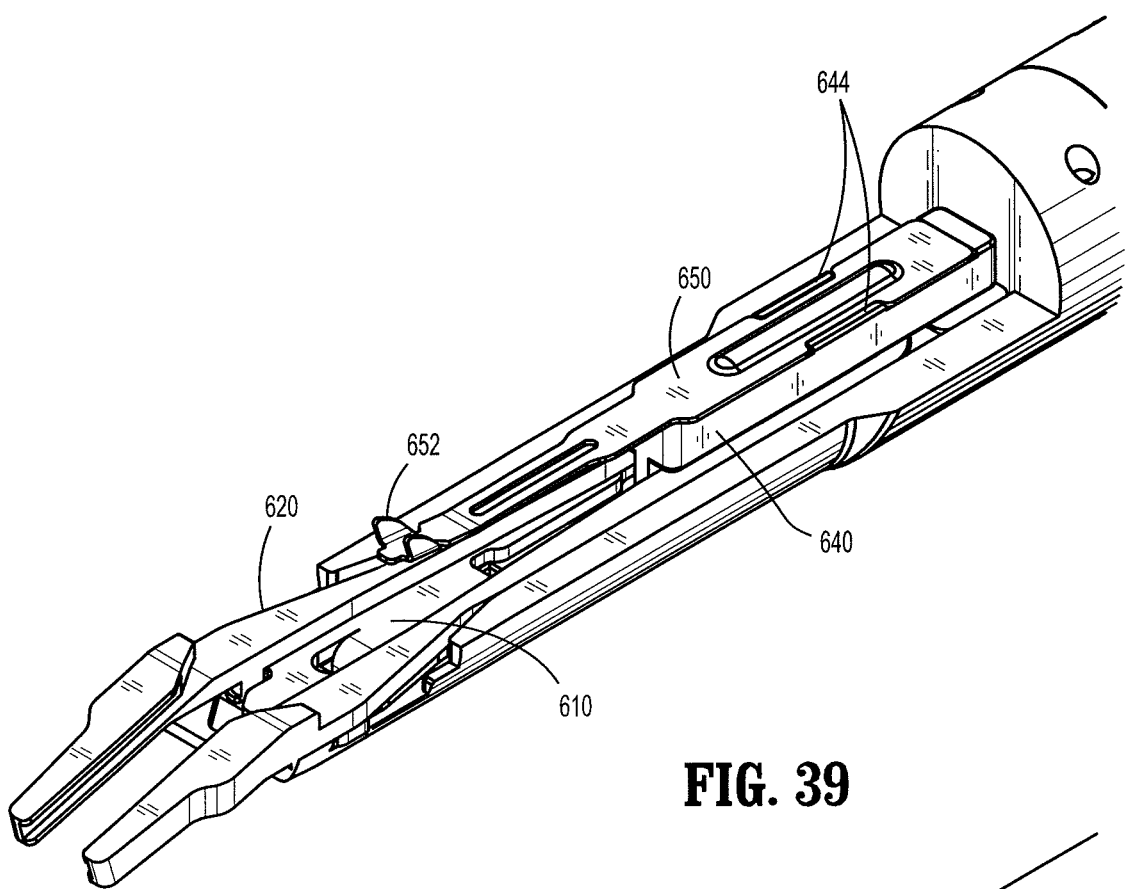
FIG. 39 is a perspective view of the housing of FIG. 36 including the distal member and the clip pusher in position.

With reference to FIG. 38, a cam spring 600 is located within the spring slot 570 of the housing 560 such that the finger 612 of the cam plate 610 is disposed distal of cam spring 600.

Figure 30:
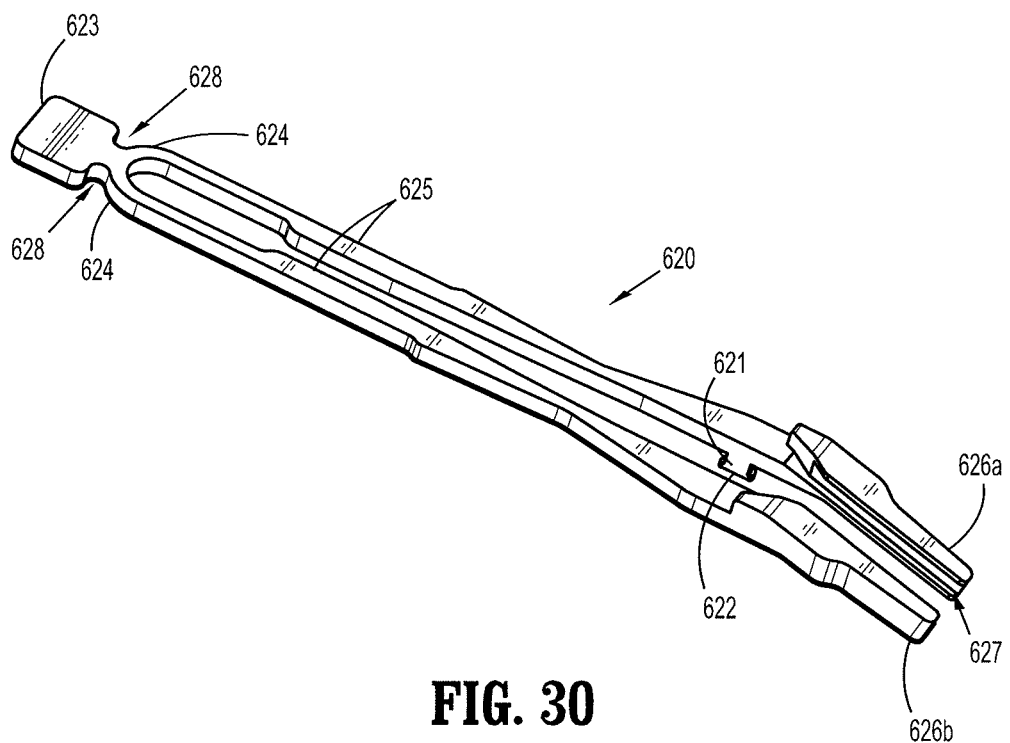
FIG. 30 is a perspective view of a jaw structure of the clip cartridge of FIG. 27.
Figure 36:
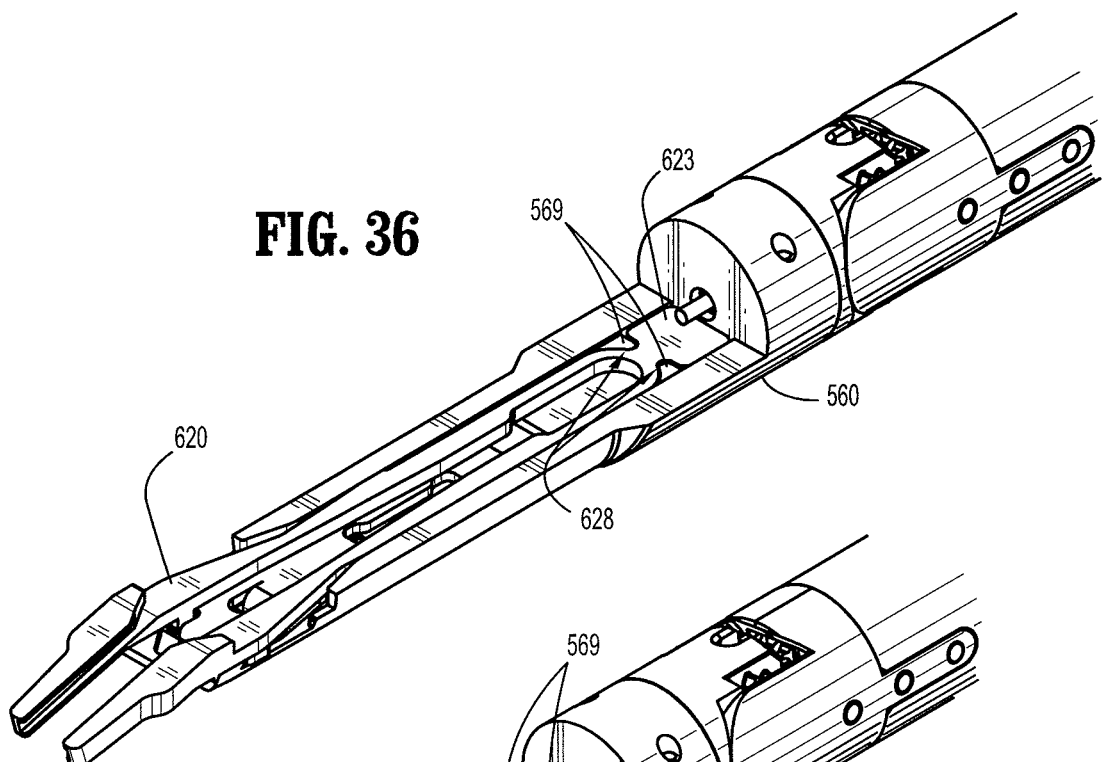
FIG. 36 is a perspective view of the housing coupled to the knuckle of the clip cartridge.

With reference to FIGS. 27 and 30, the jaw structure 620 includes a locking tab 623, a pair of legs 625, and a pair of jaws 626. A pair of lock recesses 628 is defined between the locking tab 623 and the pair of legs 625. The lock recesses 628 extend inward from side edges thereof to form a pair of locking shoulders 624. With reference to FIG. 36, the locking recesses 628 act to secure the jaw structure 620 along the first recessed surface 567 of the housing 560, by providing space for the inward projecting locks 569. The inward projecting locks 569 act upon the locking block 623 and the locking shoulders 624 to prevent longitudinal movement of the jaw structure 620 with respect to the housing 560.

Each of the pair of legs 625 extends proximally from the respective locking shoulder 624 parallel with the second longitudinal 'X2' axis. The pair of jaws 626 is formed at the distal ends of the legs 625 and includes a first jaw 626a and a second jaw 626b. Each jaw 626 extends at an angle from the respective leg 635 to form an angle with the second longitudinal 'X2' axis. The clip axis 'W' of each clip 580 is substantially parallel to a longitudinal axis of each of the first and second jaws 526a, 526b. Each jaw 626 defines a channel 627 along an inner section that is sized to accept a portion of the clip leg 582a, 582b therein. One of the clip legs 582a, 582b is retained in the channel 627 of the first jaw 626a and the other clip leg 582a, 582b is retained in the channel 627 of the second jaw 626b.

The jaw assembly or structure 620 is supported on and extends distally from between the cover 590 and the housing 560. The jaw structure 620 includes a first jaw 626a and a second jaw 626b that are moveable between a spaced apart position and an approximated position.

Figure 31:
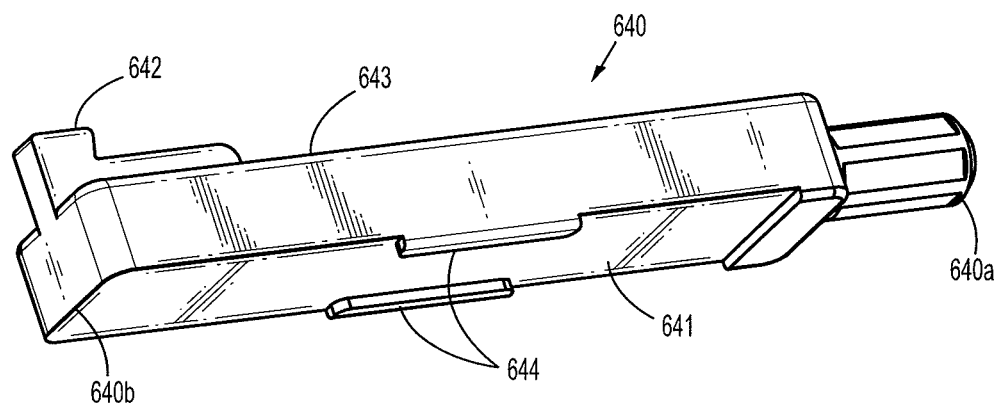
FIG. 31 is a perspective view of a block member of the clip cartridge of FIG. 27.

Referring to FIGS. 27 and 31, the movement of the cam plate 614 is provided by the block member 640. With reference to FIG. 31, the block member 640 includes a pair of rails 644 extending from a surface thereof, and a finger 642 extending from a surface opposite rails 644 at a location proximate a distal end 640b of the block member 640. The finger 642 is sized to extend between the jaw legs 624, 625 and into the dog bone shaped aperture 611 of the camming plate 610.

Figure 44:
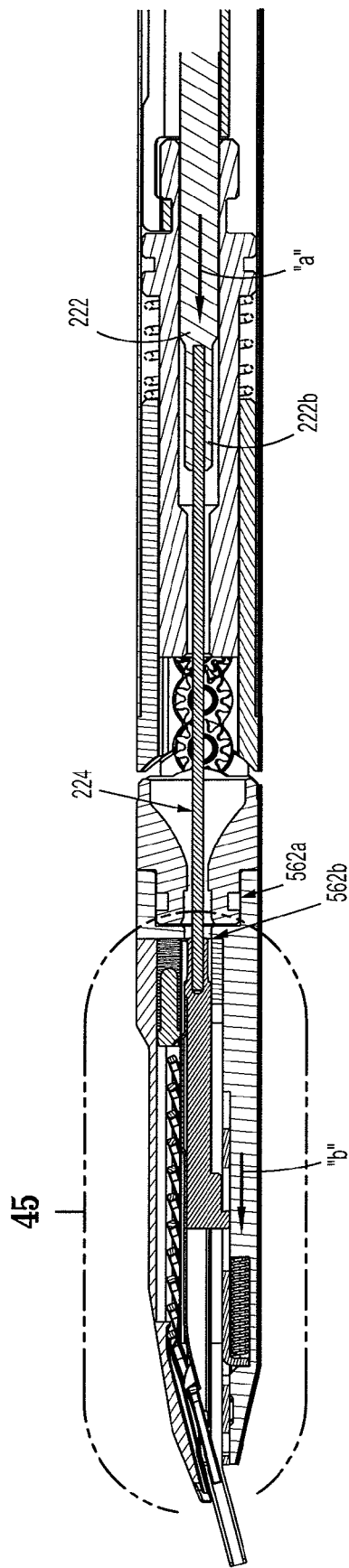
FIG. 44 is an longitudinal cross-sectional view of the clip cartridge, illustrating a clip being loaded during a first stage of operation.
Figure 45:
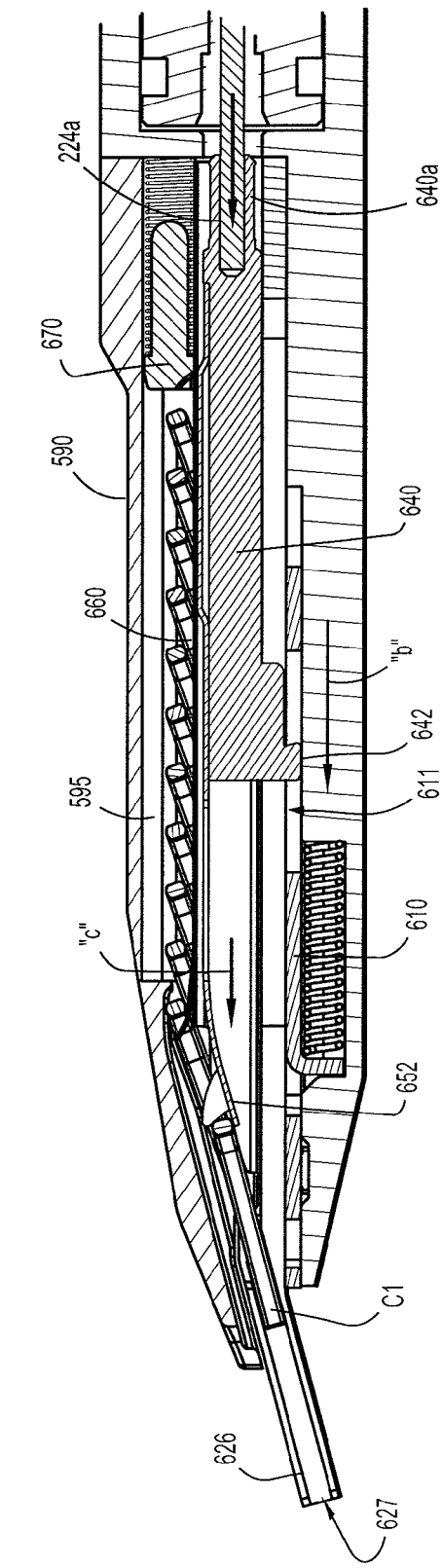
FIG. 45 is an enlarged longitudinal cross-sectional view of the clip cartridge as indicated in FIG. 44, illustrating the clip being loaded during the first stage of operation.

With reference to FIGS. 31 and 44-45, a proximal end 640a of the block member 640 is connected with the distal end 224b of the drive cable 224. As a result, advancement or retraction of the drive cable 224 advances or retracts, respectively, the block member 640 along the second longitudinal 'X2' axis. Proximal movement or retraction of the block member 640 will cause the finger 642 thereof to abut a proximal end 611a of the dog bone shaped aperture 611 of camming plate 610 and will in turn pull the camming plate 610 proximally. In a proximal position, as seen in FIGS. 49 and 50, the cam aperture 614 presents the separator 615 of camming plate 610, having a tapered end 615a, between the posts 621 of jaw structure 620 to separate the posts 621 and to open the jaws 626.

Meanwhile, distal movement or advancement of the block member 640 will cause the finger 642 to abut a distal end 611b of the dog bone shaped aperture 611 of camming plate 610 and will in turn push the camming plate 610 distally. In a distal position, as seen in FIG. 51, the camming surfaces 616, of cam aperture 614 of camming plate 610, force the posts 621 of the jaw structure 620 together to close the jaws 626. A longitudinal length of the finger 642 is less than a length of the dog bone shaped aperture 611 to thereby allow the finger 642 of block member 640 to move a predetermined distance before engaging and moving the camming plate 610.

Figure 32:
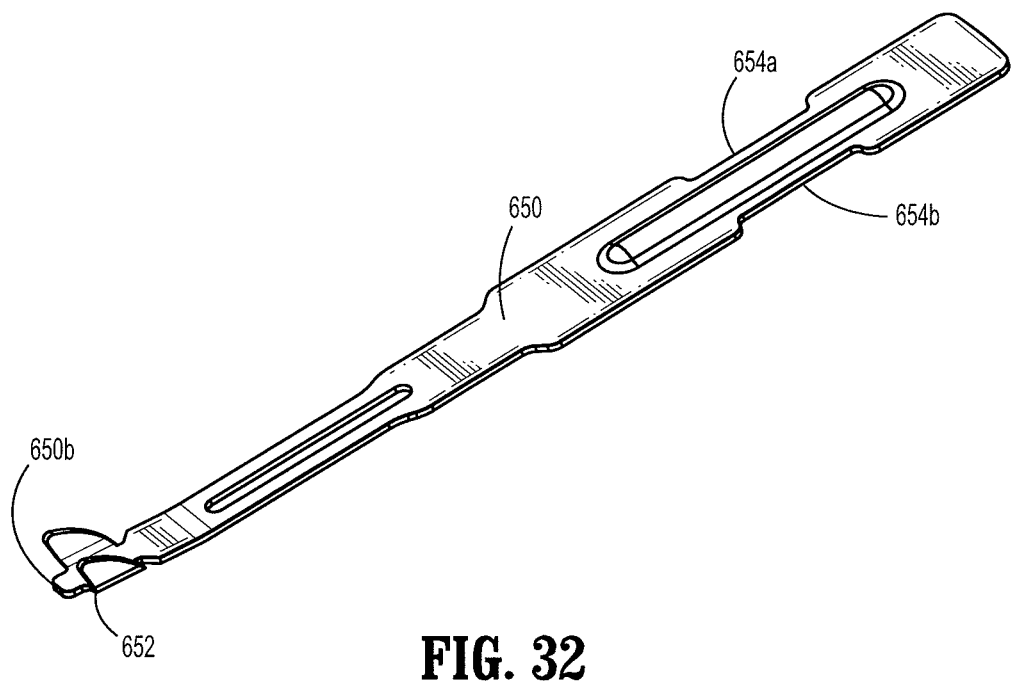
FIG. 32 is a perspective view of a clip pusher of the clip cartridge of FIG. 27.

With reference to FIGS. 27 and 32, a feed bar 650 is provided for longitudinal movement relative to cover 590 in order to advance individual clips 580 into jaws 626. As seen in FIG. 32, to facilitate the insertion of the clip 580 into jaws 626, feed bar 650 is provided with the pusher 652 at its distal end 650b, which is configured to advance an individual clip 580 out of the stack of clips 580 and into jaws 626.

The pusher 652 is sized and shaped to selectively engage/move (i.e., distally advance) a distal-most clip "C1" (FIGS. 42 and 43) of the clips 580 into the jaws 626. The feed bar defines a pair of recess 654a, 654b along each side edge thereof that are sized and shaped to accept the rails 644a, 644b of the block member 640 to mate the feed bar 650 and the block member 640. Turning to FIGS. 44-48, it is understood that a movement of the block member 640 causes a movement of the feed bar 650 in the same direction and in the same magnitude.

With reference to FIGS. 27 and 39-41, the feed bar 650 is slidably disposed under the clip carrier 660. The clip carrier 660 is shaped and sized to retain the plurality of surgical clips 580 thereon. It should be noted that clip carrier 660 and jaw structure 620 do not move longitudinally relative to housing 560.

Figure 33:
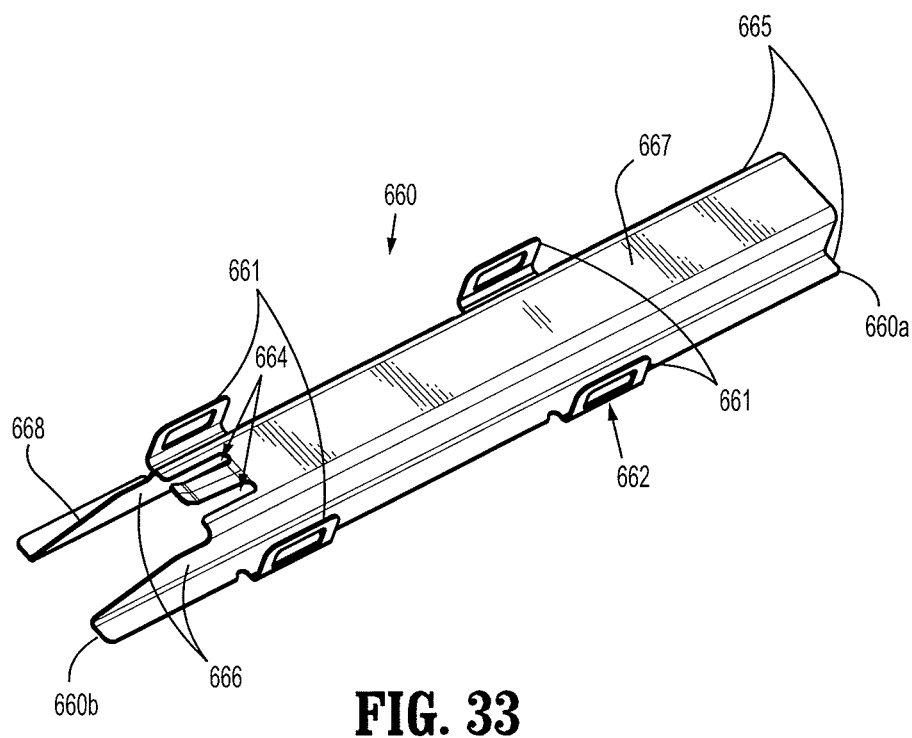
FIG. 33 is a perspective view of a clip follower of the clip cartridge of FIG. 27.

Referring to FIG. 33, the clip carrier 660 includes a distal pair of slots 664 sized and shaped to receive the pusher 652 of feed bar 650 therein. The clip carrier 660 is formed with a 'hat' shaped transverse cross-sectional profile, consisting of a center platform 667, two vertical walls 666 projecting downward from the center platform 667, and a horizontal wall 665 projecting outward from each of the vertical walls 666. Each of the horizontal walls 665 includes two longitudinally spaced retainers 661 that project upward along an outside edge. Each of the retainers 661 defines an opening 662 therethrough. A ramp section 668 about a distal end 660b allows the center platform 667 to be shorter than the horizontal walls 665.

Figure 40:
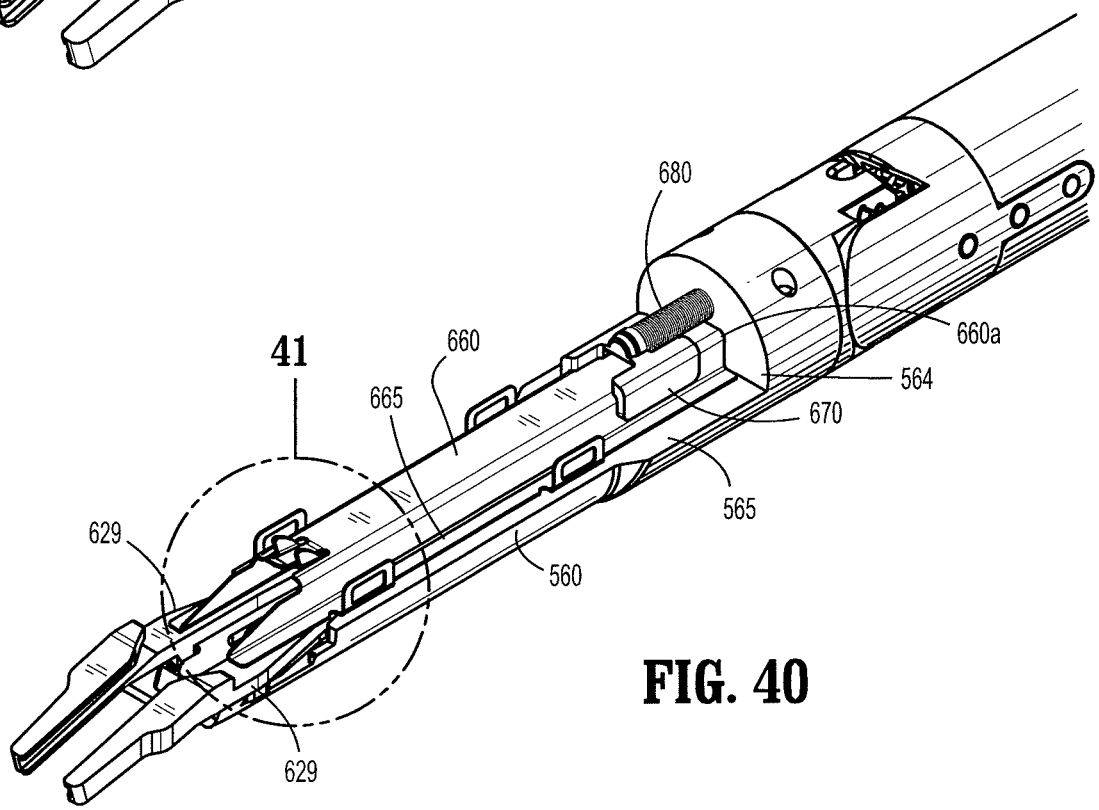
FIG. 40 is a perspective view of the housing of FIG. 39 with the addition of the clip carrier and clip follower thereon.

As shown in FIG. 40, a proximal end 660a of the clip carrier 660 is located against the perpendicular surface 564 of the housing 560 and the horizontal walls 665 sit upon the horizontal walls 565 of the housing 560. The ramp section 668 extends the clip carrier 660 partially over a flared out section 629 of the legs 625 of the jaw structure 620. The ramp section 668 forms substantially the same angle with respect to the second longitudinal 'X2' axis as the jaws 626.

Figure 34:
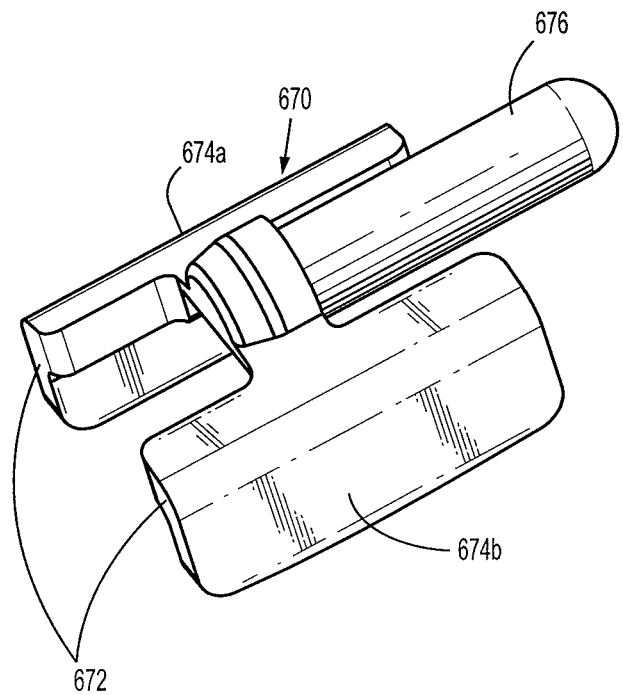
FIG. 34 is a perspective view of a clip carrier of the clip cartridge of FIG. 27.

With reference to FIGS. 27, 34, and 40, the clip follower 670 sits on top of the clip carrier 660. As shown in FIG. 34, the clip follower 670 includes an abutment surface 672 for engagement with the stack of clips 580 and includes two aims 674a, 674b for engagement about the clip carrier 660. The clip follower 670 includes a proximally extending post 676 sized to fit inside of follower spring 680. With reference to FIG. 42, the clip follower 670 is positioned behind the stack of clips 580 on the clip carrier 660 to advance the stack of clips 580 through surgical clip applier 100 as the distal-most clip is fired.

The clip follower 670 is biased distally by the follower spring 680 to urge the stack of clips 580 distally along the clip carrier 660. The cover 590 overlies the clip carrier 660 and is configured to retain and guide advancement of the follower 670, the follower spring 680, and the stack of clips 580 therein.

Figure 35:
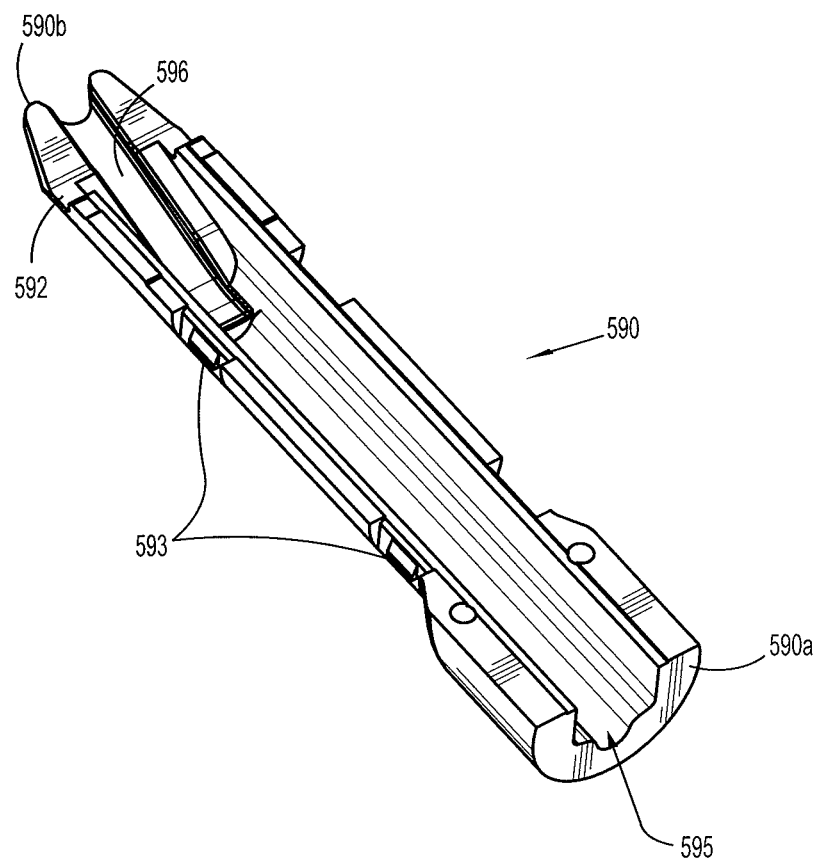
FIG. 35 is a bottom perspective view of a cover of the clip cartridge of FIG. 27.

As seen in FIGS. 27 and 35, the cover 590 of clip cartridge 550 has a substantially semi-cylindrical body 591 and a nose 592. Two pairs of securing protrusions 593 extend radially outward along each side of the semi-cylindrical body 591 of cover 590. Each securing protrusion 593 is sized and shaped to fit into and project through the openings 662 in the retainers 661 of the clip carrier 660. The cover 590 defines a longitudinal passage 595 therealong.

With reference to FIG. 45, the clip carrier 660 forms an elongated clip channel with the inner surface of the longitudinal passage 595 of the cover 590 for retaining the plurality of clips 580, as shown in stacked manner above the clip carrier 660 in FIGS. 40-43. To direct the clips 580 traversing along the clip channel and into the jaws 626, a ramped inner surface 596 is provided at a distal end 590b of cover 590 along the nose 592 to assist in directing surgical clips 580 into jaws 626.

The proximal end 590a of cover 590 is shaped to abut the perpendicular surface 564 of the housing 560.

With reference to FIGS. 44-48, the operation of the clip cartridge 550 will now be discussed. Initially, jaws 626 are placed about a vessel "V." As seen in FIG. 44, actuation of the trigger 208 (see FIG. 5A) causes distal movement of the drive assembly 220 (see FIG. 5A) and drive rod 222, represented by the direction arrow 'a'. The distal movement of drive rod 222 causes distal advancement of drive cable 224 which in turn causes the advancement of the block member 640, represented by the direction arrow 'b'. Referring to FIG. 45, the distal movement of the block member 640 causes a distal advancement of the feed bar 650, represented by the direction arrow 'c'. As the block member 640 is moved distally, the finger 642 thereof abuts against a reduced width portion of the dog bone shaped recess 611 to force the feed bar 650 distally. As the feed bar 650 is advanced distally, the pusher 652 of feed bar 650 forces a distal-most clip 'C1' distally and in-between the jaw members 626, as illustrated by the direction arrow 'd' in FIG. 46. During a further advancement of the block member 640, the finger 642 of the block member 640 travels along the dog bone shaped recess 611 of the cam plate 610 thereby maintaining the cam plate 610 stationary in a distal-most position, as seen in FIGS. 40 and 50.

Figure 48:
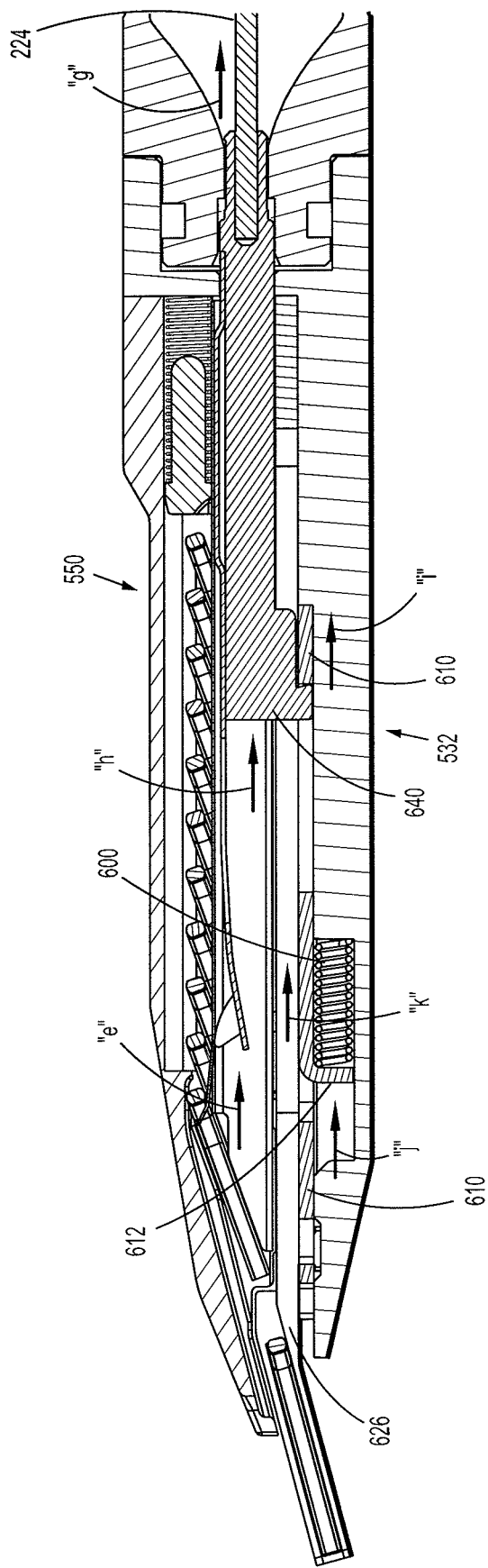
FIG. 48 is an longitudinal cross-sectional view of the clip cartridge, illustrating the forming of the loaded clip during a third stage of operation.

Referring to FIGS. 47 and 48, with distal-most clip "C1" loaded in jaw members 626, retraction of the drive rod 222 as a result of a release of trigger 208, represented by the direction arrow 'g', causes a retraction or a proximal movement of the block member 640 and of the pusher 652 of feed bar 650, as illustrated by direction arrow 'e'. As the feed bar 650 is returned to the initial or starting position, the pusher 652 is forced down toward the center of the clip cartridge 550 by a ramped edge 653 of the pusher 652 riding across the next clip in the stack of clips 580. Referring to FIG. 48, the ramped edge 653 also allows the pusher 652 to be positioned under the clip carrier 660, while the block member 640 continues to move proximally from the initial starting position, represented by the direction arrow 'h'. As the block member 640 moves proximally from the initial starting position, the finger 642 abuts and acts against the reduced width portion of the dog bone shaped recess 611 to force the cam plate 610 to move proximally, represented by the direction arrow 'i'. As the cam plate 610 moves proximally, the finger 612 of the cam plate 610 moves proximally, represented by direction arrow 'j' to compress the cam spring 600, represented by the direction arrow 'k'.

With reference to FIGS. 49-52, the forming of the clip 'C1" about a blood vessel will now be discussed. The interconnected cam plate 610 and jaw structure 626, as discussed earlier is shown in FIG. 49. With the jaws 626, having a clip 'C1' loaded therein and being placed about the blood vessel, the cam plate 610 is forced proximally by the proximally moving block member 640 to cause the camming surface 616 (see FIG. 27) of jaws 626 to act against the posts 621 of the jaw structure 626. As the camming surface 616 of camming aperture 614 abuts each of the posts 621 of the jaw structure 626, the posts 621 are forced together to form the clip 'C1' about the blood vessel, as illustrated in FIG. 52.

As the trigger 208 continues to open to withdraw drive rod 222, block member 640 is further pulled in the proximal direction until finger 642 thereof is pulled through the reduced width portion of the dog bone shaped recess 611 of the cam plate 610 at which time cam spring 600 is permitted to expand and act on finger 612 of cam plate 610 to move cam plate 610 distally and open jaw structure 626.

In this manner, a single complete stroke of trigger 208 results in a feeding of a clip "C1" into the jaws 626 and a forming of the loaded clip by the jaws 626. Such a firing sequence can be accomplished with the second longitudinal axis "X2" of the end effector 500 either axially aligned with or angled with respect to the first longitudinal axis "X1" of the first tubular member 302 of the shaft assembly 300.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A surgical clip applying apparatus for application of surgical clips to body tissue, the apparatus comprising:
    a housing;
    a drive assembly at least partially positioned within the housing;
    a shaft assembly extending distally from the housing and having a first tubular member and a second tubular member located distally from the first tubular member, the first tubular member defining a longitudinal axis, the second tubular member supporting a plurality of surgical clips and configured to distally advance each single clip of the plurality of surgical clips, individually, to form the single clip of the plurality of surgical clips upon each single firing of the surgical clip applying apparatus, the first tubular member and the second tubular member being pivotally connected through a common pivot axis, the pivot axis being perpendicular to the longitudinal axis;
    wherein the second tubular member includes a jaw assembly having a pair of juxtaposed jaws, the jaw assembly having a spaced apart condition for entirely receiving a single unformed clip between the pair of jaws, and an approximated condition wherein the pair of jaws form the single clip disposed therebetween, wherein the second tubular member defines a longitudinal axis, and wherein the pair of jaws are approximated in a direction transverse to the longitudinal axis of the second tubular member; and
    an articulation mechanism operatively connected between the first tubular member and the second tubular member, the articulation mechanism including:
        a gear rack having a plurality of teeth longitudinally placed thereon, the gear rack located within the first tubular member; and
        at least one gear operatively connected with the gear rack located within the first tubular member; and
        a gear segment extending proximally from the second tubular member, the gear segment being fixed with respect to the second tubular member, the gear segment being operatively connected with the at least one gear to pivot the second tubular member about the pivot axis.

2. The surgical clip applying apparatus according to claim 1, wherein the articulation mechanism pivots the second tubular member about the pivot axis at an angle of up to 90° from the longitudinal axis.

3. The surgical clip applying apparatus according to claim 1, further comprising a rotation mechanism, the rotation mechanism including a dial and a band located about a proximal portion of the drive assembly, the dial defining an internal passage and an inner surface, the band defining a contoured outer surface configured to receive and transmit a rotational force from the inner surface of the dial to the portion of the drive assembly.

4. The surgical clip applying apparatus according to claim 3, wherein the dial is slidably coupled with the band to permit longitudinal movement of the drive assembly with respect to the dial.

5. The surgical clip applying apparatus according to claim 1, wherein the drive assembly includes a flexible cable to transfer both a translational force and a rotational force into the second tubular member.

6. The surgical clip applying apparatus according to claim 1, wherein the second tubular member includes two substantially parallel gear segments.

7. The surgical clip applying apparatus according to claim 1, wherein the second tubular member includes a clip cartridge containing a plurality of clips disposed therein.

8. The surgical clip applying apparatus according to claim 1, further comprising a rotation mechanism, the rotation mechanism being operatively connected with and providing a rotational force to the jaw assembly.

9. The surgical clip applying apparatus according to claim 1, wherein the articulating mechanism includes a control knob being rotatable to pivot the second tubular member.

10. A surgical clip applying apparatus for application of surgical clips to body tissue, the apparatus comprising:
    a housing;
    a drive assembly at least partially located within the housing;
    a shaft assembly extending distally from the housing and having a first tubular member and a second tubular member located distally from the first tubular member, the first tubular member defining a first longitudinal axis and being configured to rotate about the first longitudinal axis, the second tubular member supporting a plurality of surgical clips and configured to distally advance each single clip of the plurality of surgical clips, individually, to form the single clip of the plurality of surgical clips upon each single firing of the surgical clip applying apparatus, the first tubular member and the second tubular member being connected through a common pivot axis, the second tubular member defining a second longitudinal axis, the second tubular member being rotatable about the second longitudinal axis, the second tubular member including a geared segment extending proximally from a proximal portion thereof, the drive assembly extending through the first tubular member and partially into the second tubular member;
    wherein the second tubular member includes a jaw assembly having a pair of juxtaposed jaws, the jaw assembly having a spaced apart condition for entirely receiving a single unformed clip between the pair of jaws, and an approximated condition wherein the pair of jaws form the single clip disposed therebetween, wherein the pair of jaws are approximated in a direction transverse to the second longitudinal axis; and
    a rack extending along a portion of the longitudinal axis, the rack being located within the first tubular member and configured to reciprocate along the first longitudinal axis, the rack being operatively connected with the geared segment to pivot the second tubular member about the pivot axis.

11. The surgical clip applying apparatus according to claim 10, wherein the second tubular member is configured to pivot about the pivot axis at an angle of up to 90° from the first longitudinal axis.

12. The surgical clip applying apparatus according to claim 10, further comprising a rotation mechanism, the rotation mechanism including a dial and a band located about a proximal portion of the drive assembly, the dial defining an internal passage and an inner surface, the band defining a contoured outer surface configured to receive and transmit a rotational force from the inner surface of the dial to the proximal portion of the drive assembly.

13. The surgical clip applying apparatus according to claim 12, wherein the dial is slidably coupled with the band to permit longitudinal movement of the drive assembly with respect to the dial.

14. The surgical clip applying apparatus according to claim 10, wherein the drive assembly includes a flexible cable to transfer both a translational force and a rotational force into the second tubular member.

15. The surgical clip applying apparatus according to claim 10, wherein the second tubular member includes a clip cartridge containing a plurality of clips disposed therein.

16. The surgical clip applying apparatus according to claim 10, further comprising a rotation mechanism, the rotation mechanism operatively connected with and providing a rotational force to the jaw assembly.

17. The surgical clip applying apparatus according to claim 16, wherein the rotation mechanism is operatively connected with the drive assembly to provide a rotational force to the distal portion of the second tubular member.

18. The surgical clip applying apparatus according to claim 10, wherein the articulating mechanism includes a control knob being rotatable to retract the rack proximally and to extend the rack distally.

* * * * *